US006537552B1

(12) United States Patent
Minion et al.

(10) Patent No.: US 6,537,552 B1
(45) Date of Patent: Mar. 25, 2003

(54) VACCINE ADJUVANT

(75) Inventors: F. Chris Minion, Ames, IA (US); Sreekumar A. Menon, Philadelphia, PA (US); Gregory G. Mahairas, Seattle, WA (US)

(73) Assignee: Iowa State University Research Foundation, Ames, IA (US)

( * ) Notice: Subject to any disclaimer, the term of this patent is extended or adjusted under 35 U.S.C. 154(b) by 0 days.

(21) Appl. No.: 09/692,064

(22) Filed: Oct. 19, 2000

Related U.S. Application Data
(60) Provisional application No. 60/160,429, filed on Oct. 19, 1999.

(51) Int. Cl.$^7$ .................. A61K 39/02; A61K 39/04; A61K 45/00; A01N 63/03; C12N 1/00

(52) U.S. Cl. .................. 424/190.1; 424/248.1; 424/264.1; 424/278.1; 424/93.3; 435/870; 435/863

(58) Field of Search .................. 424/190.1, 264.1, 424/487, 92; 435/6, 91.2

(56) References Cited

U.S. PATENT DOCUMENTS
5,252,328 A * 10/1993 Faulds et al. .................. 424/92

FOREIGN PATENT DOCUMENTS
| WO | WO 98/44119 | 10/1998 | ........... C12N/15/31 |
| WO | WO 99/24577 | 5/1999 | ........... C12N/15/31 |

OTHER PUBLICATIONS

Andersen et al., "Recall of Long–Lived Immunity to Mycobacterium tuberculosis Infection in Mice," The Journal of Immunology 154:3359–3372, 1995.
Francois–Xavier Berthet et al., "A Mycobacterium tuberculosis operon encoding ESAT–6 and a novel low–molecular–mass culture filtrate protein (CFP–10)," Microbiology 144:3195–3203, 1998.
Brandt et al., "Key Epitopes on the ESAT–6 Antigen Recognized in Mice During the Recall of Protective Immunity to Mycobacterium tuberculosis," The Journal of Immunology 157:3527–3533, 1996.
Buddle et al., "Differentiation between Mycobacterium bovis BCG–Vaccinated and M. bovis–Infected Cattle by Using Recombinant Mycobacterial Antigens," Clinical and Diagnostic Laboratory Immunology 6(1):1–5, Jan. 1999.
Elhay et al., "Delayed–type Hypersensitivity Responses to ESAT–6 and MPT64 from Mycobacterium tuberculosis in the Guinea Pig," Infection and Immunity 66(7):3454–3456, Jul. 1998.
Harboe et al., "Evidence for Occurrence of the ESAT–6 Protein in Mycobacterium tuberculosis and Virulent Mycobacterium bovis and for Its Absence in Mycobacterium bovis BCG," Infection and Immunity 64(1):16–22, Jan. 1996.
Harboe et al., "B–Cell Epitopes and Quantification of the ESAT–6 Protein of Mycobacterium tuberculosis," Infection and Immunity 66(2):717–723, Feb. 1998.
Kamath et al., "Differential Protective Efficacy of DNA Vaccines Expressing Secreted Proteins of Mycobacterium tuberculosis," Infection and Immunity 67(4):1702–1707, Apr. 1999.
Lalvani et al., "Human cytolytic and interferon γ–secreting CD8+ T lymphocytes specfic for Mycobacterium tuberculosis," Proc. Natl. Acad. Sci. USA 95:270–275, 1998.
Lyashchenko et al., "Diversity of Antigen Recognition by Serum Antibodies in Experimental Bovine Tuberculosis," Infection and Immunity 66(11):5344–5349, Nov. 1998.
Mustafa et al., "Comparison of Antigen–Specific t–Cell Responses of Tuberculosis Patients using Complex or Single Antigens of Mycobacterium tuberculosis," Scand. J. Immunol. 48:535–543, 1998.
Pais et al., "Analysis of T cells recruited during delayed–type hypersensitivity to purified protein derivative (PPD) versus challenge with tuberculosis infection," Immunology 95:69–75, 1998.
Philipp et al., "Physical mapping of Mycobacterium bovis BCG Pasteur reveals differences from the genome map of Mycobacterium tuberculosis H37Rv and from M. bovis," Microbiology 142:3135–3145, 1996.
Pollock and Andersen, "The Potential of the ESAT–6 Antigen Secreted by Virulent Mycobacteria for Specific Diagnosis of Tuberculosis," The Journal of Infectious Diseases 175:1251–4, 1997.
Pollock and Andersen, "Predominant Recognition of the ESAT–6 Protein in the First Phase of Infection with Mycobacterium bovis in Cattle," Infection and Immunity 65(7):2587–2592, Jul. 1997.
Ravn et al., "Human T Cell Responses to the ESAT–6 Antigen from Mycobacterium tuberculosis," The Journal of Infectious Diseases 179:637–45, 1999.
Sørensen et al., "Purification and Characterization of a Low–Molecular–Mass T–Cell Antigen Secreted by Mycobacterium tuberculosis," Infection and Immunity 63(5):1710–1717, May 1995.
Ulrichs et al., "Differential T cell responses to Mycobacterium tuberculosis ESAT6 in tuberculosis patients and healthy donors," Eur. J. Immunol. 28:3949–3958, 1998.
Williams et al., "Identification of Murine B–Cell and T–Cell Epitopes of *Escherichia coli* Outer Membrane Protein F with Synthetic Polypeptides," Infect. Immun. 68(5):2535–2545, 2000.

* cited by examiner

Primary Examiner—Lynette R. F. Smith
Assistant Examiner—Khatol S Shahnan-Shah
(74) Attorney, Agent, or Firm—Fish & Richardson P.C.

(57) ABSTRACT

The invention features fusion agents such as fusion proteins that are useful for the treatment of and prevention from diseases that are susceptible to the effects of cellular (Th1 type) immune responses. Also encompassed by the invention are nucleic acids encoding the fusion proteins of the invention, vectors containing the nucleic acids, and cells containing the vectors. The invention includes methods of making and using the fusion agents of the invention.

8 Claims, 7 Drawing Sheets

```
ATGAAGAAAAAGCAAGAAATTCTTAAGACTAACTTCGCTTACACTAGCGCCTTTTCGGTTTTTACCACTCTTATTCAGC
TGGATGTTTGCAAAAAAATTCTTTGCTTCAGAGTAAATTATTTAGCACTAGGCGATTCGCTAACAGCTGGATTTAATGAAG
AAACATACCGTGATTTCAAGGTACTTAGATAAAGATGGTAATTAAGCGGTCAATCTTATCCTGCTTATTTGCTTATTAT
CTACAAAAACTTAATAAGAATTCACTGTTTCTTATGATAATTTGCAATTTCTGGACAACAACAGAAAAACTGACTTACCT
TCTTAATCCAACCAAATATCCAAATGGAAAAATGAGCGATAATCCTTTAGTTACAAACTATTCAGGAAATGAAAAATATAATG
AAATAGGTTCTGTTTTTGGTGATTTTAATAAGGATTCCTATCCTGGTTTAGTCGAAAAGTTAAGAAAGCAAACCTTTGACA
ATGTCAGTGGGAGCTAATGATCCTTTTTTAGCAATTTTTAATGAATTTAAAAAATGAGCAAGTATAATAAACCAAAATCAGA
GGAAGCAAAAAATTACTAGATCCAAATGAAAGAGCGAATTTCCTGGCAGAAAAAGGAATGCTTTTAAAAGCGGAAGTCAATA
AAAAAATTGAAGAAATAAAACACAAATCTTGATAATTTAATTAAAGAATTAAAGGCGCTTAATCCAAAATTAAGTATAAATTTA
ATTGGATATAAATTGCCAAATTCCGGTTTATTAAGATTTTAAAATATCTTTATATACTTATGCAAAAATTGAAACGGACTT
TATCAATGAAATTCCCGAAAAAATTAACAAAATTATTCGTGAAAGCGCCATTAAAAATAAGGTAAATTATATGATGTCTATG
ATAAAAGTATTTGAAATGATTCTGATAAAATTTAATGGCGAAAAAATTTGACTTCCACCCTTCAATTCAAGGTTATAAAAA
ATTGCTCACCAACTTTGTTAAAACTGACCAAGAAGAAAAAGATGATTCTAATGCTGAAGAGCTAAAAATACTACAAATTT
CGATGATTTGATGAGAATAAACCGACTTATTCCAAAGTTATTGACCTAAGTGTTTTGCAAAATCAAATAAAGAATTTCTTG
AAAAATTAAACGAAAATAAGCAAACTAGTGAATTTATTGCTCAAAAAATCCACTTTGACACCGATCAAGAAGCTGCAATCAAA
GACGACAAACGCACTTTTGGAAATATAGTTCGAGAAATTGTATCTTTACCAATCTTCGATAATTTGATTTTAGAGAGTTAAT
ACCTGTTAAAAATCCGTTTGTAAAGCAATTATTAGGAAAACCAGCTGGTTCTCTTATAAAGATATCGAAC
AACTCGAAAATAAAGTGAAAGATTACGCAAGACTAATATCAAGAGAATTAAAAGAATTCAAAAATGTCACCTCAAATACTATTTCTGACACTAAG
GTAGCATTTTTGCTGAATTAAACACTAAGTCCATTTGATTTAACTAAATAAAAGACAGTGCTACATTTAAAATTTAATGAATCTCAAACCAGAAC
AAATGCAATACTAAGTCCATTTGATTTAACTAAATAAAAGACAGTGCTACATTTAAAATTTAATGAATCTCAAACCAGAAC
AAATATTAACTTTACTAGGCCTAAGTAAAACCCCTTCAGTTCCTAAACCTGAAAAAACCAAAAGATCAAAGTTCGAAGCCACAA
ACAGATACTTCTAGTCAAAAACAAGAAAAGCGGAACAAGTTCAACAGATTCAACAAAAGCTACAACTGAAAACCAAAAACCGGC
TGAGCAAACAGATTCTTCTGAGCAATCAAGTACCGAGCCTAAATCAAACTAA
```

IgG1　　　　　　　IgG2a

SEQUENCE LISTING

<160> NUMBER OF SEQ ID NOS: 9

<210> SEQ ID NO 1
<211> LENGTH: 1878
<212> TYPE: DNA
<213> ORGANISM: Mycoplasma hyopneumoniae
<220> FEATURE:
<221> NAME/KEY: CDS
<222> LOCATION: (1)...(1875)

<400> SEQUENCE: 1

| | | | | | | | | | | | | | | | | |
|---|---|---|---|---|---|---|---|---|---|---|---|---|---|---|---|---|
| atg | aag | aaa | aaa | gca | aga | aaa | ttc | tta | aga | cta | act | tcg | ctt | aca | cta | 48 |
| Met | Lys | Lys | Lys | Ala | Arg | Lys | Phe | Leu | Arg | Leu | Thr | Ser | Leu | Thr | Leu | |
| 1 | | | | 5 | | | | | 10 | | | | | 15 | | |

| gcg | cct | ttt | tcg | gtt | ttt | acc | act | ctt | att | tca | gct | gga | tgt | ttg | caa | 96 |
|---|---|---|---|---|---|---|---|---|---|---|---|---|---|---|---|---|
| Ala | Pro | Phe | Ser | Val | Phe | Thr | Thr | Leu | Ile | Ser | Ala | Gly | Cys | Leu | Gln | |
| | | | 20 | | | | | 25 | | | | | 30 | | | |

| aaa | aat | tct | ttg | ctt | tca | gaa | gta | aat | tat | tta | gca | cta | ggc | gat | tcg | 144 |
|---|---|---|---|---|---|---|---|---|---|---|---|---|---|---|---|---|
| Lys | Asn | Ser | Leu | Leu | Ser | Glu | Val | Asn | Tyr | Leu | Ala | Leu | Gly | Asp | Ser | |
| | | 35 | | | | | 40 | | | | | 45 | | | | |

| cta | aca | gct | gga | ttt | aat | gaa | gaa | aca | tac | cgt | gat | ttt | caa | ggt | act | 192 |
|---|---|---|---|---|---|---|---|---|---|---|---|---|---|---|---|---|
| Leu | Thr | Ala | Gly | Phe | Asn | Glu | Glu | Thr | Tyr | Arg | Asp | Phe | Gln | Gly | Thr | |
| 50 | | | | | 55 | | | | | 60 | | | | | | |

| tta | gat | aaa | gat | ggt | aat | tta | agc | ggt | caa | tct | tat | cct | gct | tat | ttt | 240 |
|---|---|---|---|---|---|---|---|---|---|---|---|---|---|---|---|---|
| Leu | Asp | Lys | Asp | Gly | Asn | Leu | Ser | Gly | Gln | Ser | Tyr | Pro | Ala | Tyr | Phe | |
| 65 | | | | 70 | | | | | 75 | | | | | 80 | | |

| gct | tat | tat | cta | caa | aaa | ctt | aat | aag | aat | tca | ctt | gtt | tct | tat | gat | 288 |
|---|---|---|---|---|---|---|---|---|---|---|---|---|---|---|---|---|
| Ala | Tyr | Tyr | Leu | Gln | Lys | Leu | Asn | Lys | Asn | Ser | Leu | Val | Ser | Tyr | Asp | |
| | | | 85 | | | | | 90 | | | | | 95 | | | |

| aat | ttg | gca | att | tct | ggg | aca | aca | aca | gaa | aac | tga | ctt | tac | ctt | ctt | 336 |
|---|---|---|---|---|---|---|---|---|---|---|---|---|---|---|---|---|
| Asn | Leu | Ala | Ile | Ser | Gly | Thr | Thr | Thr | Glu | Asn | * | Leu | Tyr | Leu | Leu | |
| | | 100 | | | | | 105 | | | | | 110 | | | | |

| aat | cca | acc | aaa | tat | cca | aat | gga | aaa | atg | agc | gat | aat | cct | tta | gtt | 384 |
|---|---|---|---|---|---|---|---|---|---|---|---|---|---|---|---|---|
| Asn | Pro | Thr | Lys | Tyr | Pro | Asn | Gly | Lys | Met | Ser | Asp | Asn | Pro | Leu | Val | |
| | | | 115 | | | | | 120 | | | | | 125 | | | |

| aca | aac | tat | tca | gga | aat | gaa | aaa | tat | aat | gaa | ata | ggt | tct | gtt | ttt | 432 |
|---|---|---|---|---|---|---|---|---|---|---|---|---|---|---|---|---|
| Thr | Asn | Tyr | Ser | Gly | Asn | Glu | Lys | Tyr | Asn | Glu | Ile | Gly | Ser | Val | Phe | |
| | | 130 | | | | | 135 | | | | | 140 | | | | |

| ggt | gat | ttt | aat | aag | gat | tcc | tat | cct | ggt | tta | gtc | gaa | aaa | gtt | aag | 480 |
|---|---|---|---|---|---|---|---|---|---|---|---|---|---|---|---|---|
| Gly | Asp | Phe | Asn | Lys | Asp | Ser | Tyr | Pro | Gly | Leu | Val | Glu | Lys | Val | Lys | |
| 145 | | | | | 150 | | | | | 155 | | | | | | |

| aaa | gca | aac | ctt | ttg | aca | atg | tca | gtg | gga | gct | aat | gat | cct | ttt | tta | 528 |
|---|---|---|---|---|---|---|---|---|---|---|---|---|---|---|---|---|
| Lys | Ala | Asn | Leu | Leu | Thr | Met | Ser | Val | Gly | Ala | Asn | Asp | Pro | Phe | Leu | |
| 160 | | | | 165 | | | | | 170 | | | | | 175 | | |

| gca | att | ttt | aat | gaa | ttt | aaa | aaa | tga | gca | agt | ata | ata | aaa | cca | aaa | 576 |
|---|---|---|---|---|---|---|---|---|---|---|---|---|---|---|---|---|
| Ala | Ile | Phe | Asn | Glu | Phe | Lys | Lys | * | Ala | Ser | Ile | Ile | Lys | Pro | Lys | |
| | | | 180 | | | | | 185 | | | | | 190 | | | |

| tca | gag | gaa | gca | aaa | aaa | tta | cta | gat | cca | aat | gaa | aga | gcg | aat | ttc | 624 |
|---|---|---|---|---|---|---|---|---|---|---|---|---|---|---|---|---|
| Ser | Glu | Glu | Ala | Lys | Lys | Leu | Leu | Asp | Pro | Asn | Glu | Arg | Ala | Asn | Phe | |
| | | | 195 | | | | | 200 | | | | | 205 | | | |

| ctg | gca | gaa | aaa | gga | atg | ctt | tta | aaa | gcg | gaa | gtc | aat | aaa | aaa | att | 672 |
|---|---|---|---|---|---|---|---|---|---|---|---|---|---|---|---|---|
| Leu | Ala | Glu | Lys | Gly | Met | Leu | Leu | Lys | Ala | Glu | Val | Asn | Lys | Lys | Ile | |
| | | | 210 | | | | | 215 | | | | | 220 | | | |

| gaa | gaa | ata | aac | aca | aat | ctt | gat | aat | tta | att | aaa | gaa | tta | aag | gcg | 720 |
|---|---|---|---|---|---|---|---|---|---|---|---|---|---|---|---|---|
| Glu | Glu | Ile | Asn | Thr | Asn | Leu | Asp | Asn | Leu | Ile | Lys | Glu | Leu | Lys | Ala | |
| 225 | | | | | 230 | | | | | 235 | | | | | | |

| ctt | aat | cca | aaa | tta | agt | ata | aat | tta | att | gga | tat | aaa | ttg | cca | aat | 768 |
|---|---|---|---|---|---|---|---|---|---|---|---|---|---|---|---|---|
| Leu | Asn | Pro | Lys | Leu | Ser | Ile | Asn | Leu | Ile | Gly | Tyr | Lys | Leu | Pro | Asn | |
| 240 | | | | 245 | | | | | 250 | | | | | | | |

```
tcc ggt ttt att aag att tta aaa tat ctt tta tat act tat gca aaa      816
Ser Gly Phe Ile Lys Ile Leu Lys Tyr Leu Leu Tyr Thr Tyr Ala Lys
255                 260                 265                 270 att gaa acg gac ttt atc aat gaa att ccc gaa aaa att aac aaa att      864
Ile Glu Thr Asp Phe Ile Asn Glu Ile Pro Glu Lys Ile Asn Lys Ile
                275                 280                 285 att cgt gaa agc gcc att aaa aat aag gta aat tat att gat gtc tat      912
Ile Arg Glu Ser Ala Ile Lys Asn Lys Val Asn Tyr Ile Asp Val Tyr
            290                 295                 300 gat aaa agt att tga aat gat tct gat aaa aat tta atg gcg aaa aat      960
Asp Lys Ser Ile  *  Asn Asp Ser Asp Lys Asn Leu Met Ala Lys Asn
        305                 310                 315 ttt gac ttc cac cct tca att caa ggt tat aaa aaa att gct cac caa     1008
Phe Asp Phe His Pro Ser Ile Gln Gly Tyr Lys Lys Ile Ala His Gln
    320                 325                 330 ctt ttg tta aaa ctt gac caa gaa gaa aaa gat gat tct aat gct gaa     1056
Leu Leu Leu Lys Leu Asp Gln Glu Glu Lys Asp Asp Ser Asn Ala Glu
335                 340                 345 gag cta aaa aat act aca aat ttc gat gat ttt gat gag aat aaa ccg     1104
Glu Leu Lys Asn Thr Thr Asn Phe Asp Asp Phe Asp Glu Asn Lys Pro
350                 355                 360                 365 acc tat tcc aaa gtt att gac cta agt gtt ttt gca aaa tca aat aaa     1152
Thr Tyr Ser Lys Val Ile Asp Leu Ser Val Phe Ala Lys Ser Asn Lys
                370                 375                 380 gaa ttt ctt gaa aaa tta aac gaa aat aag caa act agt gaa ttt att     1200
Glu Phe Leu Glu Lys Leu Asn Glu Asn Lys Gln Thr Ser Glu Phe Ile
            385                 390                 395 gct caa aaa tcc act ttt gac acc gat caa gaa gct gca atc aaa gac     1248
Ala Gln Lys Ser Thr Phe Asp Thr Asp Gln Glu Ala Ala Ile Lys Asp
        400                 405                 410 gac aaa cgc act ttt gga aat ata gtt cga gaa att gta tct tta cca     1296
Asp Lys Arg Thr Phe Gly Asn Ile Val Arg Glu Ile Val Ser Leu Pro
    415                 420                 425 atc ttc gat aat ttt gat ttt aga gag tta ata cct gtt aaa aat ccg     1344
Ile Phe Asp Asn Phe Asp Phe Arg Glu Leu Ile Pro Val Lys Asn Pro
430                 435                 440                 445 ttt gta aaa gca att att aac agc tat tta ggg aaa cca gct ggt tct     1392
Phe Val Lys Ala Ile Ile Asn Ser Tyr Leu Gly Lys Pro Ala Gly Ser
                450                 455                 460 ctt ata aaa gat atc gaa caa ctc gaa aat aaa gtg aaa gat tac gca     1440
Leu Ile Lys Asp Ile Glu Gln Leu Glu Asn Lys Val Lys Asp Tyr Ala
            465                 470                 475 aga cct aat atc aag att ttc gat aca att att gac tca ttc ata aga     1488
Arg Pro Asn Ile Lys Ile Phe Asp Thr Ile Ile Asp Ser Phe Ile Arg
        480                 485                 490 aaa atg gta gca ttt ttt gct gaa tta aac act gat caa gaa ata aaa     1536
Lys Met Val Ala Phe Phe Ala Glu Leu Asn Thr Asp Gln Glu Ile Lys
    495                 500                 505 gaa ttc aaa atg tca cct caa ata cta ttt ctg aca cta aga aat gca     1584
Glu Phe Lys Met Ser Pro Gln Ile Leu Phe Leu Thr Leu Arg Asn Ala
510                 515                 520                 525 ata cta agt cca ttt gat tta act aaa tta aaa gac agt gct aca ttt     1632
Ile Leu Ser Pro Phe Asp Leu Thr Lys Leu Lys Asp Ser Ala Thr Phe
                530                 535                 540 aaa att tta atg aat ctc aaa cca gaa caa ata tta act tta cta ggc     1680
Lys Ile Leu Met Asn Leu Lys Pro Glu Gln Ile Leu Thr Leu Leu Gly
            545                 550                 555 cta agt aaa acc cct tca gtt cct aaa cct gaa aaa cca aaa gat caa     1728
Leu Ser Lys Thr Pro Ser Val Pro Lys Pro Glu Lys Pro Lys Asp Gln
        560                 565                 570
```

-continued

```
agt tcg aag cca caa aca gat act tct agt caa aaa caa gaa agc gga     1776
Ser Ser Lys Pro Gln Thr Asp Thr Ser Ser Gln Lys Gln Glu Ser Gly
    575                 580                 585 aca agt tca aca gat tca aca aaa gct aca act gaa aac caa aaa ccg     1824
Thr Ser Ser Thr Asp Ser Thr Lys Ala Thr Thr Glu Asn Gln Lys Pro
590                 595                 600                 605 gct gag caa aca gat tct tct gag caa tca agt acc gag cct aaa tca     1872
Ala Glu Gln Thr Asp Ser Ser Glu Gln Ser Ser Thr Glu Pro Lys Ser
                610                 615                 620 aac taa                                                              1878
Asn
```

<210> SEQ ID NO 2
<211> LENGTH: 625
<212> TYPE: PRT
<213> ORGANISM: Mycoplasma hyopneumoniae

<400> SEQUENCE: 2

```
Met Lys Lys Lys Ala Arg Lys Phe Leu Arg Leu Thr Ser Leu Thr Leu
 1               5                  10                  15

Ala Pro Phe Ser Val Phe Thr Thr Leu Ile Ser Ala Gly Cys Leu Gln
                20                  25                  30

Lys Asn Ser Leu Leu Ser Glu Val Asn Tyr Leu Ala Leu Gly Asp Ser
             35                  40                  45

Leu Thr Ala Gly Phe Asn Glu Glu Thr Tyr Arg Asp Phe Gln Gly Thr
     50                  55                  60

Leu Asp Lys Asp Gly Asn Leu Ser Gly Gln Ser Tyr Pro Ala Tyr Phe
 65                  70                  75                  80

Ala Tyr Tyr Leu Gln Lys Leu Asn Lys Asn Ser Leu Val Ser Tyr Asp
                 85                  90                  95

Asn Leu Ala Ile Ser Gly Thr Thr Thr Glu Asn Trp Leu Tyr Leu Leu
            100                 105                 110

Asn Pro Thr Lys Tyr Pro Asn Gly Lys Met Ser Asp Asn Pro Leu Val
        115                 120                 125

Thr Asn Tyr Ser Gly Asn Glu Lys Tyr Asn Glu Ile Gly Ser Val Phe
    130                 135                 140

Gly Asp Phe Asn Lys Asp Ser Tyr Pro Gly Leu Val Glu Lys Val Lys
145                 150                 155                 160

Lys Ala Asn Leu Leu Thr Met Ser Val Gly Ala Asn Asp Pro Phe Leu
                165                 170                 175

Ala Ile Phe Asn Glu Phe Lys Lys Trp Ala Ser Ile Ile Lys Pro Lys
            180                 185                 190

Ser Glu Glu Ala Lys Lys Leu Leu Asp Pro Asn Glu Arg Ala Asn Phe
        195                 200                 205

Leu Ala Glu Lys Gly Met Leu Leu Lys Ala Glu Val Asn Lys Lys Ile
    210                 215                 220

Glu Glu Ile Asn Thr Asn Leu Asp Asn Leu Ile Lys Glu Leu Lys Ala
225                 230                 235                 240

Leu Asn Pro Lys Leu Ser Ile Asn Leu Ile Gly Tyr Lys Leu Pro Asn
                245                 250                 255

Ser Gly Phe Ile Lys Ile Leu Lys Tyr Leu Leu Tyr Thr Tyr Ala Lys
            260                 265                 270

Ile Glu Thr Asp Phe Ile Asn Glu Ile Pro Glu Lys Ile Asn Lys Ile
        275                 280                 285

Ile Arg Glu Ser Ala Ile Lys Asn Lys Val Asn Tyr Ile Asp Val Tyr
```

```
                    290                 295                 300
Asp Lys Ser Ile Trp Asn Asp Ser Asp Lys Asn Leu Met Ala Lys Asn
305                 310                 315                 320

Phe Asp Phe His Pro Ser Ile Gln Gly Tyr Lys Lys Ile Ala His Gln
                325                 330                 335

Leu Leu Leu Lys Leu Asp Gln Glu Lys Asp Asp Ser Asn Ala Glu
            340                 345                 350

Glu Leu Lys Asn Thr Thr Asn Phe Asp Asp Phe Asp Glu Asn Lys Pro
                355                 360                 365

Thr Tyr Ser Lys Val Ile Asp Leu Ser Val Phe Ala Lys Ser Asn Lys
    370                 375                 380

Glu Phe Leu Glu Lys Leu Asn Glu Asn Lys Gln Thr Ser Glu Phe Ile
385                 390                 395                 400

Ala Gln Lys Ser Thr Phe Asp Thr Asp Gln Glu Ala Ala Ile Lys Asp
                405                 410                 415

Asp Lys Arg Thr Phe Gly Asn Ile Val Arg Glu Ile Val Ser Leu Pro
                420                 425                 430

Ile Phe Asp Asn Phe Asp Phe Arg Glu Leu Ile Pro Val Lys Asn Pro
            435                 440                 445

Phe Val Lys Ala Ile Ile Asn Ser Tyr Leu Gly Lys Pro Ala Gly Ser
        450                 455                 460

Leu Ile Lys Asp Ile Glu Gln Leu Glu Asn Lys Val Lys Asp Tyr Ala
465                 470                 475                 480

Arg Pro Asn Ile Lys Ile Phe Asp Thr Ile Asp Ser Phe Ile Arg
                485                 490                 495

Lys Met Val Ala Phe Phe Ala Glu Leu Asn Thr Asp Gln Glu Ile Lys
            500                 505                 510

Glu Phe Lys Met Ser Pro Gln Ile Leu Phe Leu Thr Leu Arg Asn Ala
        515                 520                 525

Ile Leu Ser Pro Phe Asp Leu Thr Lys Leu Lys Asp Ser Ala Thr Phe
    530                 535                 540

Lys Ile Leu Met Asn Leu Lys Pro Glu Gln Ile Leu Thr Leu Leu Gly
545                 550                 555                 560

Leu Ser Lys Thr Pro Ser Val Pro Lys Pro Glu Lys Pro Lys Asp Gln
                565                 570                 575

Ser Ser Lys Pro Gln Thr Asp Thr Ser Ser Gln Lys Gln Glu Ser Gly
            580                 585                 590

Thr Ser Ser Thr Asp Ser Thr Lys Ala Thr Thr Glu Asn Gln Lys Pro
        595                 600                 605

Ala Glu Gln Thr Asp Ser Ser Glu Gln Ser Ser Thr Glu Pro Lys Ser
    610                 615                 620

Asn
625

<210> SEQ ID NO 3
<211> LENGTH: 25
<212> TYPE: PRT
<213> ORGANISM: Homo sapiens

<400> SEQUENCE: 3

Met Ala Ile Ser Gly Val Pro Val Leu Gly Phe Phe Ile Ile Ala Val
1               5                   10                  15

Leu Met Ser Ala Gln Glu Ser Trp Ala
            20                  25
```

```
<210> SEQ ID NO 4
<211> LENGTH: 4
<212> TYPE: PRT
<213> ORGANISM: Rattus rattus

<400> SEQUENCE: 4

Lys Asp Glu Leu
 1

<210> SEQ ID NO 5
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 5
gagcagatct atgacagagc agcagtggaa tttc                                  34

<210> SEQ ID NO 6
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 6
ggcagatctc tatgcgaaca tcccagtg                                         28

<210> SEQ ID NO 7
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 7
gttggatcct gcgaacatcc cagtgacg                                         28

<210> SEQ ID NO 8
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 8
gctagatctt tgcaaaaaaa ttctttgctt tc                                    32

<210> SEQ ID NO 9
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 9
gctagatctt tagtttgatt taggctcggt ac                                    32
```

VACCINE ADJUVANT

This application claims priority of U.S. Provisional Application No. 60/160,429, filed Oct. 19, 1999 no expired, which is incorporated herein by reference in its entirety.

TECHNICAL FIELD

This invention relates to vaccines, and more particularly to vaccine adjuvants.

BACKGROUND

Immune responses to many different antigens (e.g., microbial antigens or tumor antigens), while detectable, are frequently or insufficient magnitude to afford protection against a disease process mediated by agents (e.g., infectious microorganisms or tumor cells) expressing those antigens. In such situations, it is often desirable to administer to an appropriate subject, together with the antigen, an adjuvant that serves to enhance the immune response to the antigen in the subject.

SUMMARY

The invention derives from the finding that fusion agents (e.g., fusion proteins) containing an immune enhancing domain and an immunogenic domain induced more potent Th1 type T cell responses than did the molecule contained in the immunogenic domain when administered alone to mice. A similar pattern of immune responsiveness was observed when a naked DNA construct encoding a fusion protein was administered to the mice. Thus, the invention features fusion agents containing an immune enhancing domain and an immunogenic domain. In preferred embodiments, both domains are proteins and, where they are, the relevant fusion agents are called "fusion proteins." The invention also features DNAs encoding fusion proteins, vectors containing the DNAs, cells containing the vectors, and methods of making and using the fusion agents and DNAs.

More specifically, the invention features a fusion agent comprising a first domain and a second domain. The first domain contains an immune enhancing molecule and the second domain comprises an immunogenic molecule. The immunogenic molecule can be a tumor antigen, an autoantigen, a molecule produced by a fungus, a molecule produced by a mycoplasma, a molecule produced by a yeast, a polypeptide encoded by a virus, or a molecule produced by a bacterium. The bacterium can be *Salmonella enteriditis, Listeria monocytogenes, Mycobacteria leprae, Staphylococcus aureus, Escherichia coli, Streptococcus pneumoniae, Borrelia burgdorferi, Actinobacillus pleuropneumoniae, Helicobacter pylori, Neisseria meningitidis, Yersinia enterocolitica, Bordetella pertussis, Porphyromonas gigivalis,* or a mycoplasma (e.g., *Mycoplasma hyopneumoniae*). The immune enhancing molecule is a protein or a functional fragment of the protein, e.g., *Mycobacterium tuberculosis* Early Secretory Antigenic Target 6 (ESAT-6). The immunogenic molecule can be a protein or a functional fragment of the protein, e.g., *Mycoplasma hyopneumoniae* P71 protein. In addition, the fusion agent can be a fusion protein. The fusion agent can contain one or more additional domains, each of which can contain an immune enhancing molecule or an immunogenic molecule.

The invention also encompasses a DNA encoding a fusion protein that includes an immune enhancing domain and an immunogenic domain, each with the above described characteristics. In addition, the invention includes a vector containing the DNA of the invention. The vector can contain a transcriptional regulatory element (TRE) operably linked to the DNA. Also embraced by the invention is a cell containing any of the vectors of the invention.

The invention features a method of making a fusion protein. The method involves: (a) culturing a cell of the invention in which the vector that the cell contains includes a TRE operably linked to the DNA; and (b) extracting the fusion protein from the culture.

In another aspect, the invention encompasses a method of inducing an in vitro immune response to an immunogenic molecule, the method comprising culturing the a fusion agent of the invention with a T cell and an antigen presenting cell (APC). The invention also features a method of inducing an in vivo immune response to an immunogenic molecule. This method involves delivering the fusion agent (e.g., a fusion protein of the invention) to an immune system of a subject. The delivery can involve administering the fusion agent to the subject. Alternatively, where the fusion agent is a fusion protein, the delivery can involve administering a vector of the invention to the subject. The vector can include (a) a DNA encoding the fusion protein; and (b) a TRE operably linked to the DNA. The immune response to the immunogenic molecule can be an interferon-γ producing immune response and/or an IgG2a antibody response.

Another embodiment of the invention is a DNA that includes a nucleotide sequence encoding: (a) a *Mycoplasma hyopneumoniae* P71 protein; or (b) a functional fragment of the P71 protein. In this DNA, codons encoding tryptophan in the protein or the functional fragment are not TGA codons.

"Polypeptide" and "protein" are used interchangeably and mean any peptide-linked chain of amino acids, regardless of length or post-translational modification.

As used herein, an "immune enhancing molecule" is a molecule (e.g., a polypeptide) that, when administered to a mammalian subject in the form of a fusion agent also containing an immunogenic molecule, elicits a more potent IFN-γ-producing response to the immunogenic molecule than would the immunogenic molecule administered alone to the mammalian subject. It is understood that the immune enhancing molecule, when administered to the subject in the form of the fusion agent, can also elicit an IFN-γ-producing response to itself. It is also understood that the invention is not limited by any particular mechanism of action. Thus, the cells activated to produce IFN-γ by the fusion agents can be, for example, CD4+ T cells, CD8+ T cells, macrophages, monocytes, or any other cell capable of producing IFN-γ.

As used herein, an "immunogenic molecule" is a molecule that can elicit an immune response when administered to a mammalian subject on its own and/or together with an immune enhancing molecule in the form of a fusion agent. Thus, an immunogenic molecule, as used herein, is not necessarily capable of eliciting an immune response in a mammalian subject when administered on its own to the mammalian subject.

As used herein, a "functional fragment" of an immune enhancing polypeptide that is part of a fusion agent of the invention that also contains an immunogenic molecule is a fragment of the immune enhancing polypeptide that is shorter than the full-length immune enhancing polypeptide and has at least about 10% (e.g., about 20%, about 30%, about 40%, about 50%, about 60%, about 70%, about 80%, about 90%, about 95%, about 99%, or about 100% or even more) of the ability of the immune enhancing polypeptide to facilitate a more potent IFN-γ-producing response to the immunogenic molecule than the immunogenic molecule would on its own. Methods of establishing whether a fragment of an immune enhancing polypeptide is functional are known in the art. For example, fragments of interest can be made by either recombinant, synthetic, or proteolytic digestive methods. Such fragments can then be isolated and tested for their ability to enhance a IFN-γ-producing type response by procedures described herein.

As used herein, a "functional fragment" of an immunogenic polypeptide that is part of a fusion agent of the invention that also contains an immune enhancing molecule is a fragment of the immunogenic polypeptide that is shorter than the full-length immunogenic polypeptide and has at least about 10% (e.g., about 20%, about 30%, about 40%, about 50%, about 60%, about 70%, about 80%, about 90%, about 95%, about 99%, or about 100% or even more) of the ability of the immunogenic polypeptide to stimulate an immune response to the immunogenic polypeptide. Methods of establishing whether a fragment of an immunogenic polypeptide is functional are known in the art. For example, fragments of interest can be made by either recombinant, synthetic, or proteolytic digestive methods. Such fragments can then be isolated and tested for their ability to stimulate an immune response to itself. Such testing can be performed using the fragment on its own or in the form of a fusion agent together with an immune enhancing molecule of interest. Naturally it will be necessary to do the testing in the form of a fusion agent when comparing the activities of an immunogenic polypeptide and a fragment of such a polypeptide, neither of which alone stimulate an immune response.

As used herein, "operably linked" means incorporated into a genetic construct so that expression control sequences effectively control expression of a coding sequence of interest.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., inducing immune responses in mammalian subjects, will be apparent from the following description, from the drawings and from the claims.

DESCRIPTION OF DRAWINGS

FIG. 1 is a depiction of the nucleotide sequence (SEQ ID NO:1) of cDNA encoding the P71 *Mycoplasma hyopneumoiae* protein. TGA codons encoding tryptophan in *Mycoplasma hyopneumoniae* are shown in bold.

FIG. 2 is a depiction of the amino acid sequence (SEQ ID NO:2) of the P71 *Mycoplasma hyopneumoniae* protein. Tryptophan (W) residues encoded by TGA codons in *Mycoplasma hyopneumoniae* are shown in bold.

DETAILED DESCRIPTION

Figure 3:
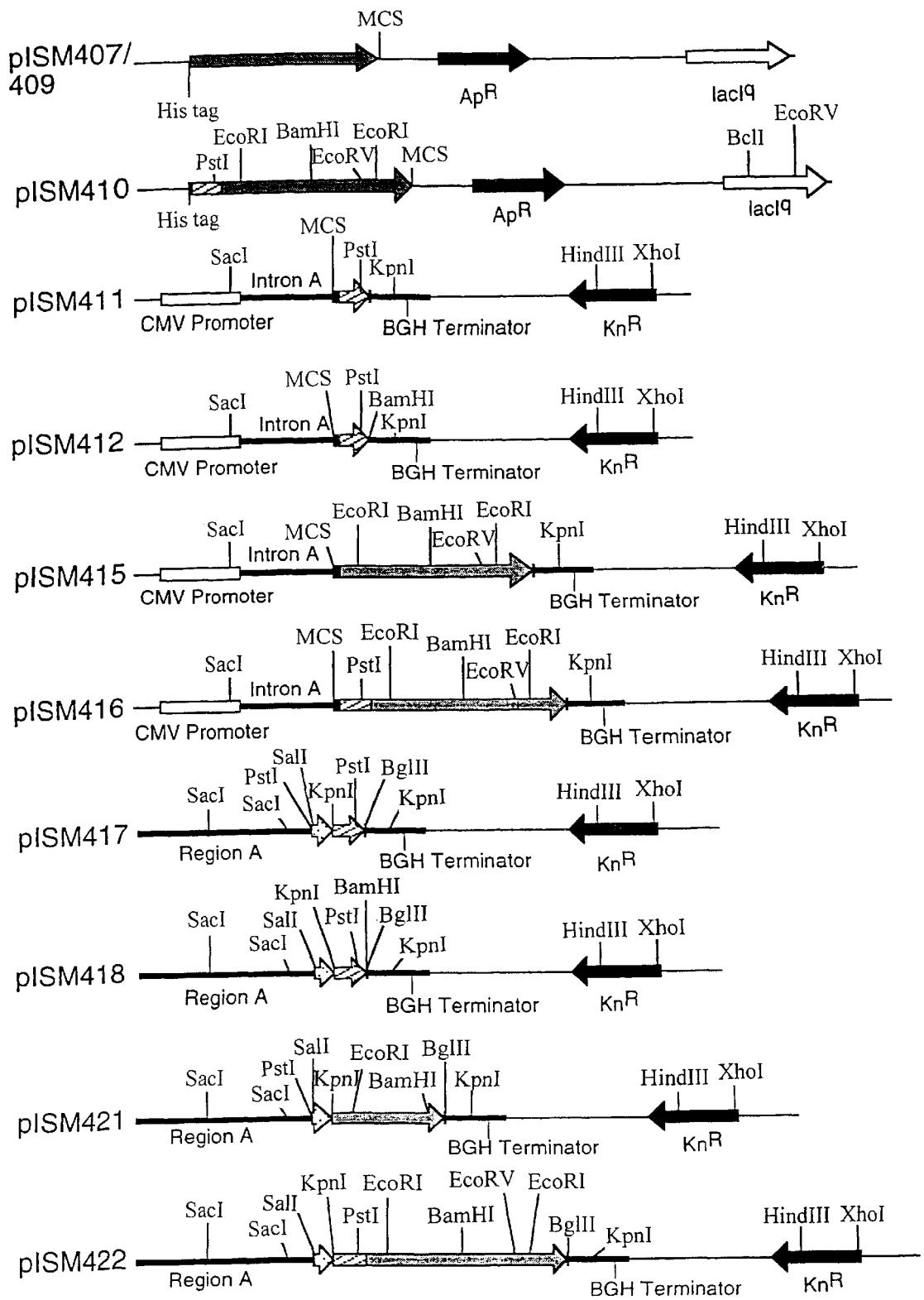
FIG. 3 is a diagram showing restriction site maps of plasmids used in the experiments described in Examples 1–4. The plasmid numbers are shown on the left. Relevant restriction sites are labeled. The black-filled arrows indicate antibiotic resistance markers, unfilled arrows indicate lacI$^q$ sequences, hatched arrows indicate ESAT-6 sequences, and gray-filled arrows indicate P71 sequences.

The invention is based on a series of experiments with (a) a fusion protein containing an immune enhancing domain and an immunogenic domain and (b) naked DNA encoding such a fusion protein. The fusion protein contained, in its immune enhancing domain, the full-length *Mycobacteria tuberculosis* Early Secretory Antigenic Target 6 (ESAT-6) polypeptide and, as the immunogenic domain, all of the P71 *M. hyopneumoniae* polypeptide except a transmembrane region and with two amino acid substitutions. This fusion protein is designated "EsP71" and the described segment of the P71 polypeptide is designated "P71d". When animals were immunized with the either EsP71 or P71d, the lymphoid cells from the former animals displayed more potent Th1-type cell responses when subsequently challenged with P71d than did lymphoid cells from the latter animals. Thus, spleen cells from mice immunized with EsP71 produced significant amounts of interferon-γ (IFN-γ) in response to P71d and but those from mice immunized with P71d produced no detectable or significantly less IFN-γ. On the other hand, higher levels of interleukin- (IL-) 10 were produced by spleen cells in response to P71d from mice immunized with P71d than were produced by spleen cells from mice immunized with EsP71. Similar results were obtained in analogous experiments comparing the IFN-γ and IL-10 producing responses to an analogous fusion protein that contained, instead of P71d, the P97 *M. hyopneumoniae* polypeptide with the responses to the P97 polypeptide. In addition, while EsP71 and P71d elicited similar IgG1 responses to P71d, EsP71 elicited stronger IgG2a responses to P71d than did P71d. Essentially the same relative pattern of IFN-γ, IL-10 and IgG2a responsiveness was seen when mice immunized with expression vectors containing nucleotide sequences encoding EsP71 or P71d were tested.

Thus, coadministration to a subject of ESAT-6 with an immunogen of choice, in the form either of a fusion protein containing ESAT-6 and the immunogen or an expression vector encoding such a fusion protein, elicits a stronger Th1 T cell response in the subject than does immunization with either the immunogen or an expression vector encoding the immunogen. There are many other molecules that would be expected to have the same Th-1-type immune response enhancing activity shown herein by ESAT-6, e.g., the major core forming outer membrane proteins (Omp) of gram negative bacteria, e.g., *E. coli*. One such Omp is the *E. coli* OmpF which was shown to polarize T helper cells toward a Th1 type response [Williams et al. (2000) Infect. Immun. 68(5):2535–2545]. Hence, the fusion agents (e.g., fusion proteins) and the DNAs of the invention can be useful in the treatment of and prophylaxis from conditions in which Th1 responses are therapeutic or preventative, respectfully. They can be useful, for example, in the treatment of or prevention from a variety of infectious diseases (e.g., those involving intracellular microbes), cancer, and autoimmune diseases such as systemic lupus erythematosus (SLE) or myasthenia gravis (MG) in which the autoimmune pathology is substantially due to antibody-mediated (i.e., Th2-mediated) effects. Furthermore, they can be used in basic scientific studies on immunity and, in particular, on factors affecting the types (e.g., Th1 versus Th2) of immune responses generated by immunization of test subjects. For example, they can be used to generate populations of T cells (clonal or non-clonal) displaying a Th1 phenotype for use in such studies or for adoptive immunotherapy.

Fusion Agents

The fusion agents of the invention have at least two domains. In a fusion agent with two domains, the first domain is an immune enhancing domain and contains a molecule that serves to direct a T cell response to the immunogenic molecule contained in the second domain in the direction of cellular immunity (i.e., a Th1-type response). The second domain contains an immunogenic molecule to which it is desired to elicit a cell-mediated (Th1-type) immune response. In fusion agents of the invention containing more than two domains, the additional domains can be immune enhancing and/or immunogenic domains.

Immune enhancing domains

Molecules to be used in immune enhancing domains can be, for example, proteins, carbohydrates, lipids, or nucleic acids. They are preferably proteins or functional fragments of such proteins. Examples of such molecules include ESAT-6 and Omps or functional fragments thereof. Methods for establishing whether a given molecule enhances the Th1 response in a subject to a prospective fusion agent immunogenic domain molecule would be known to one skilled in the art (see, e.g., Examples 3 and 4).

ESAT-6 is a potent inducer of IFN-γ [Mustafa et al. (1998) Scand. J. Immunol. 48:535–543]. In addition, multiple subregions of the ESAT-6 polypeptide have been shown. For example, an HLA-DR restricted epitope and an HLA-DPB1*0401 restricted eiptope were mapped to amino acids 42 to 52 and amino acids 73 to 81, respectively. In addition, the C-terminal end of ESAT-6 was shown to be recognized by human IFN-γ secreting CD8+ T cells [Lalvani et al. (1998) Proc. Natl. Acad. Sci. U.S.A. 95:270–275]. Furthermore, synthetic peptides containing amino acids 1 to 20 and amino acids 10 to 30 of ESAT-6 were presented by various HLA-DR molecules and thereby elicited IFN-γ production by activated CD4+ T cells [Ulrichs et al. (1998) Eur. J. Immunol. 28:3949–3958]. Because of its potent IFN-γ inducing activity, it occurred to the inventors that ESAT-6 might be able to stimulate the production of IFN-γ in response to a molecule co-administered with it, and in particular, to a molecule physically associated with it.

The invention also includes artificial immune enhancing domains. Thus, for example, an immune enhancing domain can contain one or more different molecules, e.g., any of the above-listed polypeptides or functional fragments thereof. Thus, for example, a given immune enhancing domain can contain whole or subregions of both ESAT-6 and Omp. The relevant subregions would be those with the ability to enhance a Th1 response to the molecule in the immunogenic domain. In addition, a particular immune enhancing domain can contain one or more (e.g., two, three, four, six, eight, 10, 15 or 20) repeats of one or more (e.g., two, three, four, six, eight, 10, 15 or 20) immune enhancing subregions of one or more (e.g., two, three, four, or six) polypeptides that enhance a Th1 response to an immunogenic molecule of interest.

The amino acid sequence of protein immune enhancing molecules can be identical to the wild-type sequence of the appropriate polypeptide. Alternatively, the immune enhancing molecule can contain deletions, additions, or substitutions. All that is required is that the immune enhancing molecule have at least 5% (e.g., 10%, 20%, 30%, 40%, 50%, 60%, 70%, 80%, 90%, 95%, 99%, 100% or even more) of the ability of the wild-type polypeptide to stimulate a Th1 type immune response. Methods of comparing the relative ability of two or more molecules to enhance a particular immune response are known in the art. Such methods can be, for example, simple adaptions of the experiments described in Examples 3 and 4. Substitutions will preferably be conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Immunogenic domains

The immunogenic domains of the fusion agents of the invention can contain any molecule against which it is desirable to induce a significant Th1 type immune response. The molecules can be proteins, carbohydrates, lipids, or nucleic acids. They are preferably proteins or functional fragments of proteins.

The molecules of the immunogenic domains (the "immunogenic molecules") can be molecules produced by any of a wide variety of infectious microorganisms (e.g., intracellular microorganisms) such as bacteria, fungi, yeast, mycoplasma, or viruses. Examples of appropriate microorganisms include those from, without limitation, *Salmonella enteriditis, Listeria monocytogenes, M. leprae, Staphylococcus aureus, Escherichia coli, Streptococcus pneumoniae, Borrelia burgdorferi, Actinobacillus pleuropneumoniae, Helicobacter pylori, Neisseria meningitidis, Yersinia enterocolitica, Bordetella pertussis, Porphyromonas gigivalis,* mycoplasma, *Histoplasma capsulatum, Cryptococcus neoformans, Chlamydia trachomatis, Candida*

*albicans, Plasmodium falciparum, Entamoeba histolytica, Toxoplasma brucei, Toxoplasma gondii, Leishmania major,* human immunodeficiency virus 1 and 2, influenza virus, measles virus, rabies virus, hepatitis virus A, B, and C, rotaviruses, papilloma virus, respiratory syncytial virus, feline immunodeficiency virus, feline leukemia virus, and simian immunodeficiency virus. Mycoplasmal species include: *Mycoplasma hyopneumoniae* (swine); *M. hyorhinis* (swine); *M. hyosynoviae* (swine); *M. gallisepticum* (avian); *M. synoviae* (avian); *M. meleagridis* (avian); *M. gallinarum* (avian); *M. bovis* (bovine/caprine); *M. bovoculi* (bovine); *M. dispar* (bovine); *M. capricolum* (caprine/bovine); *M. mycoides* subspecies *mycoides* (Large Colony (LC) and small colony (SC)) (ovine/caprine); *M. mycoides* subspecies *capri* (ovine/caprine); *M. agalactiae* (caprine/ovine); *M. pneumoniae* (human); *M. genitalium* (human); *M. penetrans* (human); *M. fermentans* (human); *M. hominis* (human); and all *Ureaplasma urealyticum* serotypes (human). Relevant immunogenic molecules include, without limitation, the B subunit of heat labile enterotoxin of *E. coli* [Konieczny et al. (2000) FEMS Immunol. Med. Microbiol. 27(4):321–332], heat-shock proteins, e.g., the *Y. enterocolitica* heat shock protein 60 [Konieczny et al. (2000) supra; Mertz et al. (2000) J. Immunol. 164(3):1529–1537] and *M. tuberculosis* heat-shock proteins hsp60 and hsp70, the *Chlamydia trachomatis* outer membrane protein [Ortiz et al. (2000) Infect. Immun. 68(3):1719–1723], the *B. burgdorferi* outer surface protein [Chen et al. (1999) Arthritis Rheum. 42(9):1813–1823], the *L. major* GP63 [White et al. (1999) Vaccine 17(17):2150–2161 (and published erratum in Vaccine 17(20–21):2755)], the *N. meningitidis* meningococcal serotype 15 PorB protein [Delvig et al. (1997) Clin. Immunol. Immunopathol. 85(2);134–142], the *P. gigivalis* 381 fimbrial protein [Ogawa, (1994) J. Med. Microbiol. 41(5) :349–358], and the *E. coli* outer membrane protein F [Williams et al. (2000) Infect. Immun. 68(5):2535–2545]. Mycoplasmal immunogenic proteins include the P1 protein of *M. penumoniae* and its homologs in *M. genitalium* and *M. gallisepticum*, the pMGA gene family in *M. gallisepticum*, surface lipoproteins that undergo antigenic variation such as the VSP proteins in *M. bovis*, the VLP proteins in *M. hyorhinis*, P78 in *M. fermentans*, and the VAA proteins in *M. hominis*. Furthermore, mycoplasmal glycolipids that play a role in pathogenesis can also be useful immunogenic molecules for the fusion agents of the invention. Alternatively, an immunogenic molecule can be a tumor antigen. As used herein, a "tumor antigen" is a molecule (e.g., a protein molecule) that is expressed by a tumor cell and either (a) differs qualitatively from its counterpart expressed in normal cells, or (b) is expressed at a higher level in tumor cells than in normal cells. Thus, a tumor antigen can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart. Appropriate tumors include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such ovarian cancer, vaginal cancer, bladder cancer, testicular cancer, prostate cancer or penile cancer, bone tumors, and vascular tumors. Examples of tumor antigens include, without limitation, CEA, prostate specific antigen (PSA), MAGE (melanoma antigen) 1–4, 6 and 12, MUC (Mucin) (e.g., MUC-1, MUC-2, etc.), tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2–10, c-ERB2 (Her2/neu), EBNA (Epstein-Barr Virus nuclear antigen) 1–6, gp75, human papilloma virus (HPV) E6 and E7, p53, lung resistance protein (LRP) Bcl-2, and Ki-67. In addition, the immunogenic molecule can be an autoantigen involved in the initiation and/or propagation of an autoimmune disease, the pathology of which is largely due to the activity of antibodies specific for a molecule expressed by the relevant target organ, tissue, or cells, e.g., SLE or MG. In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens of interest include, without limitation: (a) with respect to SLE, the Smith protein, RNP ribonucleoprotein, and the SS-A and SS-B proteins; and (b) with respect to MG, the acetylcholine receptor.

The amino acid sequence of a candidate protein immunogenic molecule can be identical to the sequence of appropriate wild-type protein. Alternatively, the immunogenic molecule can contain deletions, additions, or substitutions. All that is required is that the immunogenic molecule have at least 5% (e.g., 10%, 20%, 30%, 40%, 50%, 60%, 70%, 80%, 90%, 95%, 99%, 100%, or even more) of the ability of the wild-type polypeptide to stimulate an immune response, either in the presence or in the absence of an immune enhancing domain. Substitutions will preferably be conservative substitutions (see above).

Immune enhancing and immunogenic domains can be disposed in any convenient orientation with respect to each other in the fusion proteins of the invention. Thus, for example, in a fusion protein of the invention, the immune enhancing domain can be N-terminal of the immunogenic domain or vice versa. The two domains can be immediately adjacent to each or they can be separated by a linker peptide. Linker peptides can be 1 to about 30, even 50, amino acids long and can contain any amino acids. In general, a relatively large proportion (e.g., 20%, 40%, 60%, 80%, 90%, or 100%) of the amino acid residues in the linker will be glycine and/or serine residues. Such linkers can contain, for example, one or more (e.g., two, three, four, five, six, seven, eight, nine, ten, or more) gly-gly-gly-ser (GGGS) units.

Linking of one non-protein molecule to another or of one non-protein molecule to a protein molecule can be achieved by standard chemical methods known in the art.

Smaller fusion proteins (less than 100 amino acids long) can be conveniently synthesized by standard chemical means. In addition, the fusion proteins can be produced by standard in vitro recombinant DNA techniques and in vivo recombination/genetic recombination (e.g., transgenesis), using the nucleotide sequences encoding the appropriate polypeptides or peptides. The fusion proteins can also be made by a combination of chemical and recombinant methods.

Methods well known to those skilled in the art can be used to construct expression vectors containing relevant coding sequences and appropriate transcriptional/translational control signals. See, for example, the techniques described in Sambrook et al., Molecular Cloning: A Laboratory Manual (2nd Ed.) [Cold Spring Harbor Laboratory, N.Y., 1989], and Ausubel et al., Current Protocols in Molecular Biology, [Green Publishing Associates and Wiley Interscience, N.Y., 1989].

Expression systems that may be used for small or large scale production of the fusion proteins include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention (see below); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV) or transformed with recombinant plasmid expression vectors (for example, Ti plasmid) containing fusion protein nucleotide sequences; or mammalian cell systems (for example, COS, CHO, BHK, 293, VERO, HeLa, MDCK, W138, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal, transfected with a plasmid vector or infected with a viral vector.

The fusion proteins of the invention also include those described above, but which contain additional amino acid segments. Thus the fusion proteins can contain, for example, a hydrophobic signal peptide. The signal peptide is generally immediately N-terminal of the mature polypeptide (fusion protein) but can be separated from it by one or more (e.g., 2, 3, 4, 6, 8, 10, 15 or 20) amino acids, provided that the leader sequence is in frame with the nucleic acid sequence encoding the fusion protein. The signal peptide, which is generally cleaved from proteins prior to secretion, directs proteins into the lumen of an appropriate cell's endoplasmic reticulum (ER) during translation and the proteins are then secreted, via secretory vesicles, into the environment of the cell. Useful signal peptides can be the native signal peptide of the relevant immune enhancing or immunogenic molecule or a functional fragment of the native signal peptide, i.e., a fragment of the signal peptide that substantially the same signal activity as the full-length leader. Alternatively, the signal peptide can be that of another exported polypeptide. For example, the signal peptide can have the amino acid sequence MAISGVPVLGFFIIAVLMSAQESWA (SEQ ID NO:3). In addition, the peptide sequence KDEL (SEQ ID NO:4) has been shown to act as a retention signal for the ER.

The fusion proteins of the invention can also be modified for in vivo use by the addition, at the amino- and/or carboxyl-terminal ends, of a blocking agent to facilitate survival of the relevant polypeptide in vivo. This can be useful in those situations in which the polypeptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety.

Nucleic Acids Encoding Fusion Proteins

The invention includes nucleic acids (e.g., cDNA, genomic DNA, synthetic DNA, or RNA) encoding any of the above fusion proteins of the invention. The nucleic acids can be double-stranded or single-stranded (i.e., a sense or an antisense strand). A RNA molecule can be produced by in vitro transcription. The nucleic acid molecules are not limited to coding sequences and can include some or all of the non-coding sequences that lie upstream or downstream of a particular coding sequence. The nucleic acids can have nucleotide sequences that are identical to those of nucleic acids encoding the wild-type immune enhancing and immunogenic molecules. Alternatively, they can contain codons other than wild-type codons but which, due to the degeneracy of the genetic code, encode immune enhancing or immunogenic polypeptides with amino acid sequences identical to relevant wild-type polypeptides. Furthermore, the nucleic acids can encode immune enhancing or immunogenic polypeptides (or functional fragments thereof) with any of the above described deletions, additions, or substitutions. In addition, the nucleic acids can contain nucleotide sequences encoding functional fragments of immune enhancing and/or immunogenic polypeptides.

Generally, the nucleic acids will include "hybrid genes," containing at least two portions. The first portion will encode the immune enhancing domain and second portion will encode the immunogenic domain. Where the fusion protein encoded by the nucleic acid contains more than two domains, the appropriate acid will contain a corresponding number of portions. Between the first and second portions (and any additional portions) can be codons encoding a linker (see above).

The invention also includes vectors containing the above nucleic acids. The vectors are preferably expression vectors. In the expression vectors of the invention, the nucleic acid sequence encoding a fusion protein of interest with an initiator methionine and, preferably, a signal sequence is "operably linked" to one or more transcriptional regulatory elements (TRE), e.g., a promoter or enhancer-promoter combination.

A promoter is a TRE composed of a region of a DNA molecule, typically within 100 nucleotide pairs upstream of the point at which transcription starts. Promoters are clustered around the initiation site for RNA polymerase II. Enhancers provide expression specificity in terms of time, location, and level. Unlike a promoter, an enhancer can function when located at variable distances from the transcription site, provided a promoter is present. An enhancer can also be located downstream of the transcription initiation site. The coding sequence in the expression vector is operatively linked to a transcription terminating region. To bring a coding sequence under the control of a promoter, it is necessary to position the translation initiation site of the translational reading frame of the peptide or polypeptide between one and about fifty nucleotides downstream (3') of the promoter. A list of promoters is provided in Table 1.

TABLE 1

PROMOTERS

| PROMOTER TYPE | PROMOTER ELEMENT | REFERENCES |
| --- | --- | --- |
| CONSTITUTIVE | | |
| | β-actin | Liu et al., Mol. Cell Biol. 10: 3432–40 (1990) |
| | Tubulin | Angelichio et al., Nucleic Acids Res. 19: 5037–43 (1991) |
| | CMV | see Invitrogen |
| | SV40 enhancer | see Pharmacia |
| | RSV-LTR | see Invitrogen |
| | Adenovirus enhancer | Inoue et al., Biochem Biophys Res Commun 173: 1311–6 (1990) |
| TISSUE-SPECIFIC Liver | | |
| | serum amyloid A | Li et al., Nucleic Acids Res 20: 4765–72 (1992) |
| | Phenylalanine hydroxylase | Wang et al., J Biol Chem 269: 9137–46 (1994) |
| | IGFBP-1 | Babajko et al., PNAS 90: 272–6 (1993) |
| | apolipoprotein B | Brooks et al., Mol Cell Biol 14: 2243–56 (1994) |
| | Albumin | Pinkert et al., Genes Dev 1: 268–76 (1987) |
| | Vitellogenin | Corthesy et al., Mol Endocrinol 5: 159–69 (1991) |
| | Angiotensinogen | Brasier et al., Embo J 9: 3933–44 (1990) |
| | Haptoglobin | Yang et al., Genomics 18: 374–80 (1993) |
| | PEPCK | Short et al., Mol Cell Biol 12: 1007–20 (1992) |
| | factor IX | Jallat et al., Embo J 9: 3295–301 (1990) |
| | Transferrin | Idzerda et al., Mol Cell Biol 9: 5154–62 (1989) |
| | β-fibrinogen | Dalmon et al., Mol Cell Biol 13: 1183–93 (1993) |
| | Kininogen | Chen et al., Mol Cell Biol 13: 6766–77 (1993) |
| | CRP | Toniatti et al., Mol Biol Med 7: 199–212 (1990) |
| KIDNEY | | |
| | Renin | Fukamizu et al., Biochem Biophys Res Commun 199: 183–90 (1994) |
| HEART | | |
| | Cardiac myosin light chain | Lee et al., J Biol Chem 267: 15875–85 (1992) |
| | Cardiac troponin C | Parmacek et al., Mol Cell Biol 12: 1967–76 (1992) |
| | α-cardiac myosin heavy chain | Gulick et al., J Biol Chem 266: 9180–5 (1991) |
| | MCK troponin 1 | Johnson et al., Mol Cell Biol 9: 3393–9 (1989) |
| | Atrial natriuretic factor | Rockman et al., PNAS 88: 8277–81 (1991) erratum 88(21): 9907 |
| LUNG | | |
| | pulmonary surfactant protein SP-C | Glasser et al. Am J Physiol L349–56 (1991) |
| PANCREAS/ISLET | | |
| | insulin | Dandoy et al., Nucleic Acids Res 19: 4925–30 (1991); and Selden et al., Nature 321–525–8 (1986) |
| | pancreatic amylase | Osborn et al., Mol Cell Biol 7: 326–34 (1987) |
| BRAIN/GLIA | | |
| | GFAP | Brenner et al., J Neurosci 1030–7 (1994) |
| | JCV | Henson et al., J Biol Chem 269: 1046–50 (1994) |
| | MBP | Miskimins et al., Brain Res Dev Brain Res 65: 217–21 (1992) |
| | serotonin 2 receptor | Ding et al., Brain Res Mol Brain Res 20: 181–91 (1993) |
| | myelin PO | Monuki et al., Mech Dev 42: 15–32 (1993) |
| | myelin proteolipid protein | Berndt et al. J Biol Chem 267: 14730–7 (1992) |
| INDUCIBLE A) IMMUNE SYSTEM/NATURAL | | |
| | IL-2 | Thompson et al., Mol Cell Biol 12: 1043–53 (1992) |
| | IL-4 | Todd et al., J Exp Med 177: 1663–74 (1993) |
| | IL-6 | Libermann et al., Mol Cell Biol 10: 2327–34 (1990); and Matsusaka et al., PNAS 90: 10193–7 (1993) |
| | IL-8 | Matsusaka et al., PNAS 90: 10193–7 (1993) |
| | IL-10 | Kim et al., J Immunol 148: 3618–23 (1992) |
| | TNF-α | Drouet et al., J Immunol 147: 1694–700 (1991) |
| | IL-1 | Shirakawa et al., Mol Cell Biol 13: 1332–44 (1993) |
| | M1P-1 | Grove et al., Mol Cell Biol 13: 5276–89 (1993) |
| | IFN-γ | Penix et al., J Exp Med 178: 1483–96 (1993) |
| | VCAM-1 | Iademarco et al., J Biol Chem 267: 16323–9 (1992) |
| | ICAM-1 | Voraberger et al., J Immunol 14: 2777–86 (1991) |
| | ELAM-1 | Whelan et al., Nucleic Acids Res 19: 2645–53 (1991) |
| | tissue factor | Mackman et al., J Exp Med 174: 1517–26 (1991) |

TABLE 1-continued

PROMOTERS

| PROMOTER TYPE | PROMOTER ELEMENT | REFERENCES |
|---|---|---|
| | IFN-β | Visvanathan et al., Embo J 8: 1129–38 (1989) |
| | c-jun | Muegge et al., PNAS 90: 7054–8 (1993) |
| | junB | Nakajima et al., Mol Cell Biol 13: 3017–41 (1993) |
| | c-fos | Morgan et al., Cell Prolif 25: 205–15 (1992) |
| | iNOS | Xie et al., J Exp Med 177: 1779–84 (1993) |
| | G-CSF | Shannon et al., Growth Factors 7: 181–93 (1992) |
| | GM-CSF | Miyatake et al., Mol Cell Biol 11: 5894–901 (1991) |
| B) IMMUNE SYSTEM/SYNTHETIC multiple copies of binding sites | | |
| | NF-KB | Lenardo et al., Cell 58: 227–9 (1989) |
| | NF-IL6 | Akira et al., Embo J 9: 1897–906 (1990) |
| | IL6-response element | Wegenka et al., Mol Cell Biol 13: 276–88 (1993) |
| | CRE | Brindle et al., Curr Opin Genet Dev 2: 199–204 (1992) |
| | AP-1 | Auwerx et al., Oncogene 7: 2271–80 (1992) |
| | p91/stat | Larner et al., Science 261: 1730–3 (1993) |
| | combinations of multiple NF-KB and NF-1L6 or combinations with the other elements | |
| C) EXOGENOUS/NON-MAMMALIAN | | |
| | IPTG inducible/lac repressor/operon system | see Stratagene LacSwitch ™, La Jolla, CA |
| | ecdysone-inducible promoter/ecdysone receptor | Burtis et al., Cell 61: 85–99 (1990) |
| | Na-salicylate-inducible promoter PG/regulator nahR | Yen, J Bacteriol 173: 5328–35 (1991) |
| | nalidixic acid inducible recA promoter | Rangwala et al., Biotechnology 9: 477–9 (1993) |

Suitable expression vectors include, without limitation, plasmids and viral vectors such as herpes viruses, retroviruses, vaccinia viruses, attenuated vaccinia viruses, canary pox viruses, adenoviruses, adeno-associated viruses, lentiviruses and herpes viruses, among others.

The expression vectors of the invention containing the above described coding sequences have a variety of uses. They can be used, for example, to transfect or transduce either prokaryotic (e.g., bacteria) cells or eukaryotic cells (e.g., yeast, insect, or mammalian) cells. Such cells can then be used, for example, for large or small scale in vitro production of the relevant fusion protein by methods known in the art (see above). In essence, such methods involve culturing the cells under conditions which maximize production of the fusion proteins and isolating the fusion proteins from the culture, i.e., from either cells or from the culture medium into which the fusion protein has been secreted. The transduced/transfected cells can also be used for delivery of a fusion protein to the immune system of a subject by administration of the transduced/transfected cells to the subject, as for example, in the ex vivo methods described below. Alternatively, the vector itself can be administered to the subject.

The cells of the invention can, for example, be transduced with: (a) a single expression vector containing a nucleic acid sequence (e.g., a genomic DNA sequence, a cDNA sequence, or an RNA sequence) encoding one of the above fusion proteins of the invention; (b) two (or more) vectors, each containing a coding sequence encoding a different fusion protein; or (c) a single vector containing (two more) coding sequence, each encoding a different fusion protein, and each coding sequence being separately transcribed and/or translated.

Methods of Activating an Immune Response

The invention features methods of activating an immune response in which cells of the immune system are exposed to one or more fusion agents of the invention. In the immune response activated by the fusion agent, a more potent Th1 and/or more enduring Th1 type response is elicited than is elicited by the immunogenic molecule component of the fusion agent on its own.

The methods of the invention can be performed in vitro, in vivo, or ex vivo. In vitro application of the fusion agents can be useful, for example, in basic scientific studies of immune mechanisms or for production of activated T cells for use in either studies on T cell function or, for example, passive immunotherapy.

In the in vitro methods of the invention, T cells (CD4+ and/or CD8+) obtained from a mammalian subject (see below) are cultured in with a fusion agent of the invention and antigen presenting cells (APC), preferably, but not necessarily, obtained from the same individual as the T cells. Where the APC are obtained from a different individual, the donor of the T cells and the donor of the APC will preferably express at least one major histocompatibility complex (MHC) molecule (e.g., a MHC class II molecule) in common. APC can be essentially any MHC expressing cell. They will preferably be MHC class II-expressing cells. Thus, they can be, for example, interdigitating dendritic cells (DC), macrophages, monocytes, B cells, or cell lines (clonal or non-clonal) derived from any of these cells. They can also be any cell type (e.g., fibroblasts) transfected or transduced with and expressing a polynucleotide encoding an MHC class II molecule. Such cultures can also be supplemented with one or more cytokines or growth factors such as, without limitation, IL-1, IL-2, IL-3, IL-6, IL-7, IL-12, IL-15, IFN-γ, tumor necrossis factor-α (TNF-α), granulocyte macrophage colony-stimulating factor (GM-CSF), or granulocyte-colony stimulating factor (G-CSF). The cultures can be "restimulated" as often as necessary with either the fusion agent or the immunogenic molecule component of the fusion agent alone. The cultures can also be monitored at various times to ascertain whether the desired spectrum of Th1-type cytokines and their level of production has been attained.

The fusion agents of the invention are generally useful as Th1-type immune response-stimulating therapeutics. For example, the fusion agents of the invention can be used for treatment of disease conditions characterized by immunosuppression: e.g. cancer, AIDS or AIDS-related complex, other virally or environmentally-induced conditions, and certain congenital immune deficiencies. The compounds may also be employed to increase immune function that has been impaired by the use of radiotherapy of immunosuppressive drugs such as certain chemotherapeutic agents, and therefore are particularly useful when given in conjunction with such drugs or radiotherapy. In addition, in view of the ability of the described immune enhancers (e.g., ESAT-6) to stimulate the production of especially high levels of IFN-γ, the fusion agents of the invention can be used to treat conditions involving pathologic antibody-mediated responses such as those involved in certain autoimmune diseases (e.g., SLE or MG).

The methods of the invention can be applied to a wide range of species, e.g., humans, non-human primates, horses, cattle, pigs, sheep, goats, dogs, cats, rabbits, guinea pigs, hamsters, rats, and mice.

In vivo Approaches

In one in vivo approach, the fusion agent itself is administered to the subject. Generally, the fusion agents of the invention will be suspended in a pharmaceutically-acceptable carrier (e.g., physiological saline) and administered orally or by intravenous infusion, or injected subcutaneously, intramuscularly, intraperitoneally, intrarectally, intravaginally, intranasally, intragastrically, intratracheally, or intrapulmonarily. They are preferably delivered directly to an appropriate lymphoid tissue (e.g. spleen, lymph node, or mucosal-associated lymphoid tissue (MALT)). The dosage required depends on the choice of the route of administration, the nature of the formulation, the nature of the patient's illness, the subject's size, weight, surface area, age, and sex, other drugs being administered, and the judgment of the attending physician. Suitable dosages are in the range of 0.01–100.00 μg/kg. Wide variations in the needed dosage are to be expected in view of the variety of fusion agents available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, a polynucleotide containing a nucleic acid sequence encoding a fusion protein of interest can be delivered to an appropriate cells of the animal. Expression of the coding sequence will preferably be directed to lymphoid tissue of the subject by, for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1–10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), *J. Mol. Med.* 73, 479]. Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known [Thompson et al. (1992), *Mol. Cell. Biol.* 12, 1043–1053; Todd et al. (1993), *J. Exp. Med.* 177, 1663–1674; Penix et al. (1993), *J. Exp. Med.* 178, 1483–1496]. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the fusion protein of interest with an initiator methionine and optionally a targeting sequence is operatively linked to a promoter or enhancer-promoter combination. Promoters and enhancers are described above.

Polynucleotides can be administered in a pharmaceutically acceptable carrier. Pharmaceutically acceptable carriers are biologically compatible vehicles which are suitable for administration to a human or other mammalian subject, e.g., physiological saline. A therapeutically effective amount is an amount of the polynucleotide which is capable of producing a medically desirable result (e.g., an enhanced T cell response) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This does can be repeatedly administered, as needed. Routes of administration can be any of those listed above.

Ex Vivo Approaches

In one ex vivo approach, lymphoid cells, including T cells (CD4+ and/or CD8+ T cells), are isolated from the subject and exposed to the fusion agent in vitro (see above). The lymphoid cells can be exposed once or multiply (e.g., 2, 3, 4, 6, 8, or 10 times). The pattern of cytokine production by the lymphoid cells can be tested after one or more exposures. Once the desired cytokines are being produced by the lymphoid cells, they are reintroduced into the subject via any of the routes listed herein. The therapeutic or prophylactic efficacy of this ex vivo approach is dependent on the ability of the ex vivo activated lymphocytes to either: (a) exert, directly or indirectly, a neutralizing or cytotoxic effect on, for example, infectious microorganisms, host cells infected with microorganisms, or tumor cells; or (b) actively suppress a pathogenic T cell response as, for example, in SLE or MG.

An alternative ex vivo strategy can involve transfecting or transducing cells obtained from the subject with a polynucleotide containing a fusion protein-encoding nucleotide sequence. The transfected or transduced cells are then returned to the subject. While such cells would preferably be lymphoid cells, they could also be any of a wide range of types including, without limitation, fibroblasts, bone marrow cells, macrophages, monocytes, dendritic cells, epithelial cells, endothelial cells, keratinocytes, or muscle cells in which they act as a source of the fusion protein for as long as they survive in the subject. The use of lymphoid cells would be particularly advantageous in that such cells would be expected to home to lymphoid tissue (e.g., lymph nodes or spleen) and thus the fusion protein would be produced in high concentration at the site where they exert their effect, i.e., activation of an immune response. By using this approach, as in to the above-described in vivo approach using fusion protein-encoding polynucleotides, active in vivo immunization with the fusion protein is achieved. The same genetic constructs and signal sequences described for the in vivo approach can be used for this ex vivo strategy.

The ex vivo methods include the steps of harvesting cells from a subject, culturing the cells, transducing them with an expression vector, and maintaining the cells under conditions suitable for expression of the fusion protein. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are then selected, for example, for expression of the fusion protein or of a drug resistance gene. The cells may then be lethally irradiated (if desired) and injected or implanted into the patient.

These methods of the invention can be applied to any of the diseases and species listed here. Methods to test whether a fusion agent is therapeutic for or prophylactic against a particular disease are known in the art. Where a therapeutic effect is being tested, a test population displaying symptoms of the disease (e.g., cancer patients) is treated with a test fusion agent, using any of the above described strategies. A control population, also displaying symptoms of the disease, is treated, using the same methodology, with a placebo. Disappearance or a decrease of the disease symptoms in the test subjects would indicate that the fusion agent was an effective therapeutic agent.

By applying the same strategies to subjects prior to onset of disease symptoms (e.g., presymptomatic subjects considered to likely candidates for SLE development or experimental animals in which an appropriate disease spontaneously arises, e.g., NZB mice, or can be deliberately induced, e.g., multiple murine cancers), fusion agents can be tested for efficacy as prophylactic agents, i.e., vaccines. In this situation, prevention of onset of disease symptoms is tested.

The following examples are meant to illustrate, not limit, the invention.

EXAMPLES

Example 1

Materials and Methods

Bacterial Strains and Plasmids. *Escherichia coli* strains LE392 (F$^-$ hsd514(rk$^-$, mk$^-$) lacY supE44 sup F5 galK2 galT22 trpR55 metB1λ$^-$) and TOP10 (F$^-$merA Δ(mrr–hsdRMS–mcrBC) ø80 lac ΔM15 ΔlacX74 deoR recA1 ara D139 Δ(ara–leu)7697 galU galK rspL endA1 nupG) were obtained from laboratory stocks maintained at −70° C. and were grown in Luria Bertani media. The pTrcHis B plasmid was obtained from Invitrogen, Inc. (Carlsbad, Calif.). The mammalian expression plasmid pVR1020 was a gift from Vical, Inc. Plasmids were stored at −20° C.

Figure 2:
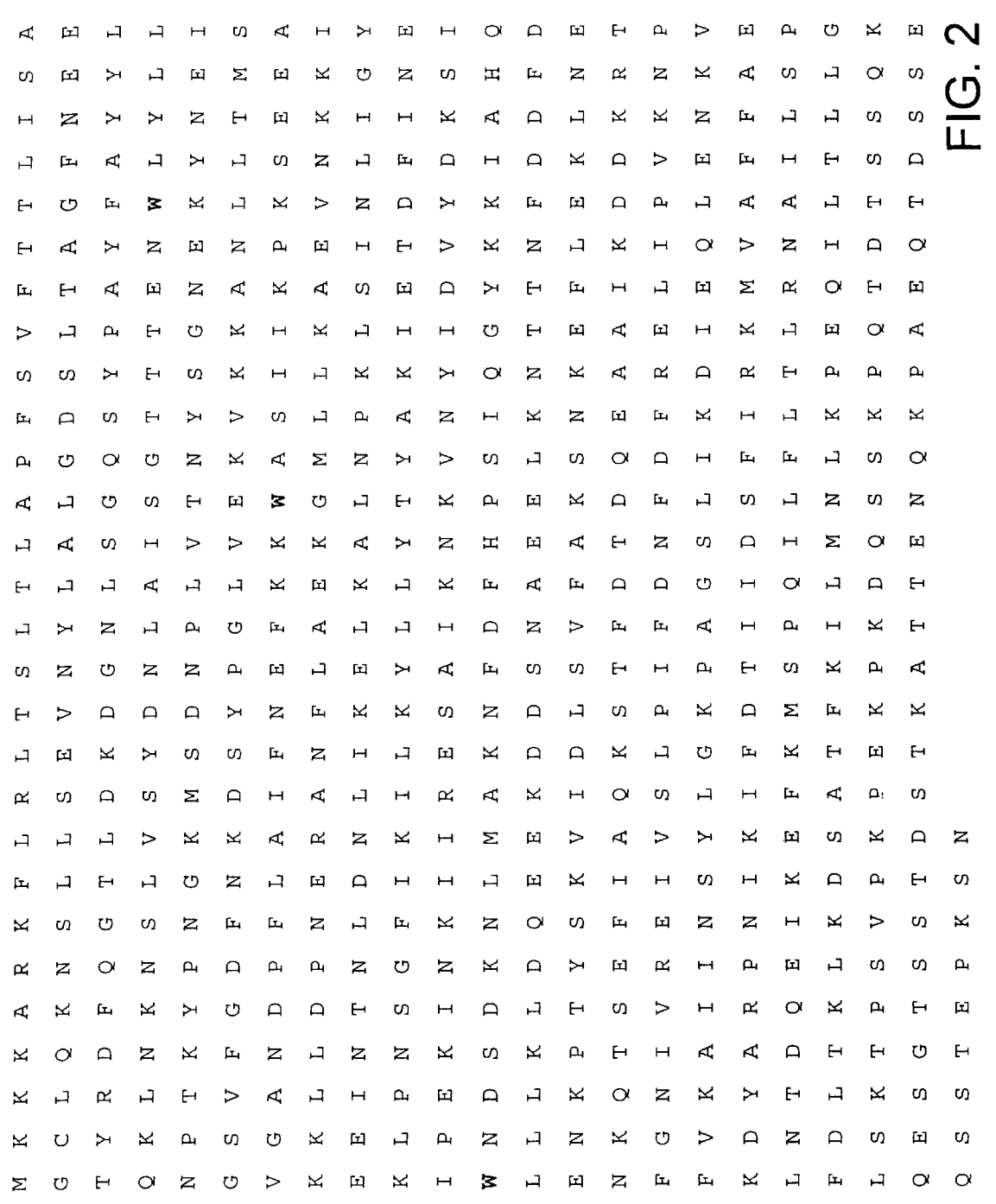

Genomic library screening and identification of P71 gene sequences. A *M. hyopneumoniae* genomic library constructed in Lambda ZAP II was screened with convalescent, challenge-protected swine sera S195 as described [Wolff et al. (1990) Science 247: 1465–68]. The cloned fragments were excised in vivo [Short et al. (1988) Nucleic Acids Res 16: 7583–600], and the resulting recombinant plasmids were subjected to restriction enzyme analysis and restriction site mapping. Five of the twelve positive clones overlapped a single chromosomal region. The gene encoded within this region was identified by deletion analysis followed by Tn1000 mutagenesis and transposon-assisted DNA sequencing [Strathmann et al. (1991) Proc Natl Acad Sci USA 88: 1247–50]. FIG. 1 shows the nucleotide sequence of cDNA encoding P71 (SEQ ID NO: 1) and FIG. 2 shows the amino acid sequence of P71 (SEQ ID NO: 2).

Plasmid Constructions. Cloning of DNA into various plasmids was accomplished following established protocols [Sambrook et al. Cold Spring Harbor, N.Y.: Cold Spring Harbor Laboratory, 1989]. The coding sequence for P71 was cloned into pTrcHis B forming pISM407, which was used for site-directed mutagenesis (described below) resulting in PISM409 which was used for the production and purification of the recombinant P71d protein used in the immunological assays. The pTrcHis B expression vector adds the following residues to the N-terminus of proteins produced by inserting an appropriate coding sequence into it: (a) an initiator methionine; (b) a Gly-Gly-Ser linker; (c) a polyhistidine (hexahistidine) sequence; and (d) an amino acid sequence whose length depends on the restriction sites used for introduction of coding sequence into the vector (27 amino acids where the BglII site is used) and includes enterokinase recognition and cleavage sites as well as an epitope (the Xpress™ epitope) recognized by the anti-Xpress antibody. The polyhistidine sequence facilitates purification of the proteins by metal affinity chromatography. Plasmid pVR1020 was used for producing DNA vaccine vectors. The orientation of cloned fragments was verified by restriction mapping or by PCR. Verification by PCR required the use of a vector-specific forward and an insert-specific reverse primer. DNA sequencing was done to verify the sequence or the reading frame wherever warranted.

Plasmid pISM403 contained the complete ESAT-6 open reading frame (ORF) with ATG start and TGA stop codons and was used to purify recombinant ESAT-6. The ESAT-6 gene was also inserted into DNA vaccine vector pVR1020 forming plasmid pISM417. To accomplish this, ESAT-6 was PCR amplified from plasmid pISM403 using primers F2Es (5'-G A G C A G A T C T A T G A C A G A G C A G C A G TGGAATTTC-3') (SEQ ID NO: 5) and R1Es (5'-GGCAGATCTCTATGCGAACATCCCAGTG-3') (SEQ ID NO: 6) and cloned into BamHI-digested pVR1020 to generate plasmid pISM417. The primer F2Es was designed to maintain the reading frame with the tissue plasminogen activator (TPA) signal sequences in pVR1020. The TPA leader peptide (encoded by the signal sequence) that is added to the N-terminus of proteins expressed by the pVR1020 expression vector is cleaved from the protein prior to transport to the cell membrane or secretion by an appropriate cell. To create vectors for producing the EsP71 fusion protein, a similar construct was made with a BamHI site downstream of ESAT-6. This was accomplished using PCR primers F2Es and R2Es (5'-GTTGGATCCTGCGAACA TCCCAGTGACG-3') (SEQ ID NO: 7) to amplify the ESAT-6 gene and clone into pVR1020 generating plasmid pISM418. This plasmid contained a BamHI site without the terminal stop codon at the 3' end of ESAT-6 allowing for protein fusion constructions. The PCR product containing the P71 structural gene (but lacking the first 92 base pairs encoding a membrane spanning domain) was generated from pISM409 using primers P71.1 (5'-GCTAGATCTTTGCAAAAAAATTCTTT GCTTTC-3') (SEQ ID NO: 8) and P71.2 (5'-GCTAGATCTTTAGTTTGATTTAGGCTCGGTAC-3') (SEQ ID NO: 9). The fragment was digested with BglII and cloned into the BamHI site of pVR1020 to generate plasmid pISM421. The structural gene for P71 was also cloned into pISM403 to generate plasmid pISM410 and into pISM418 generating plasmid pISM422, both of which contained the EsP71 fusion protein (FIG. 3). In all the EsP71 encoding constructs, there is a two codon nucleotide sequence that encodes a Gly-Ser linker between the ESAT-6 coding sequence and the P71 d coding sequence.

Figure 4:
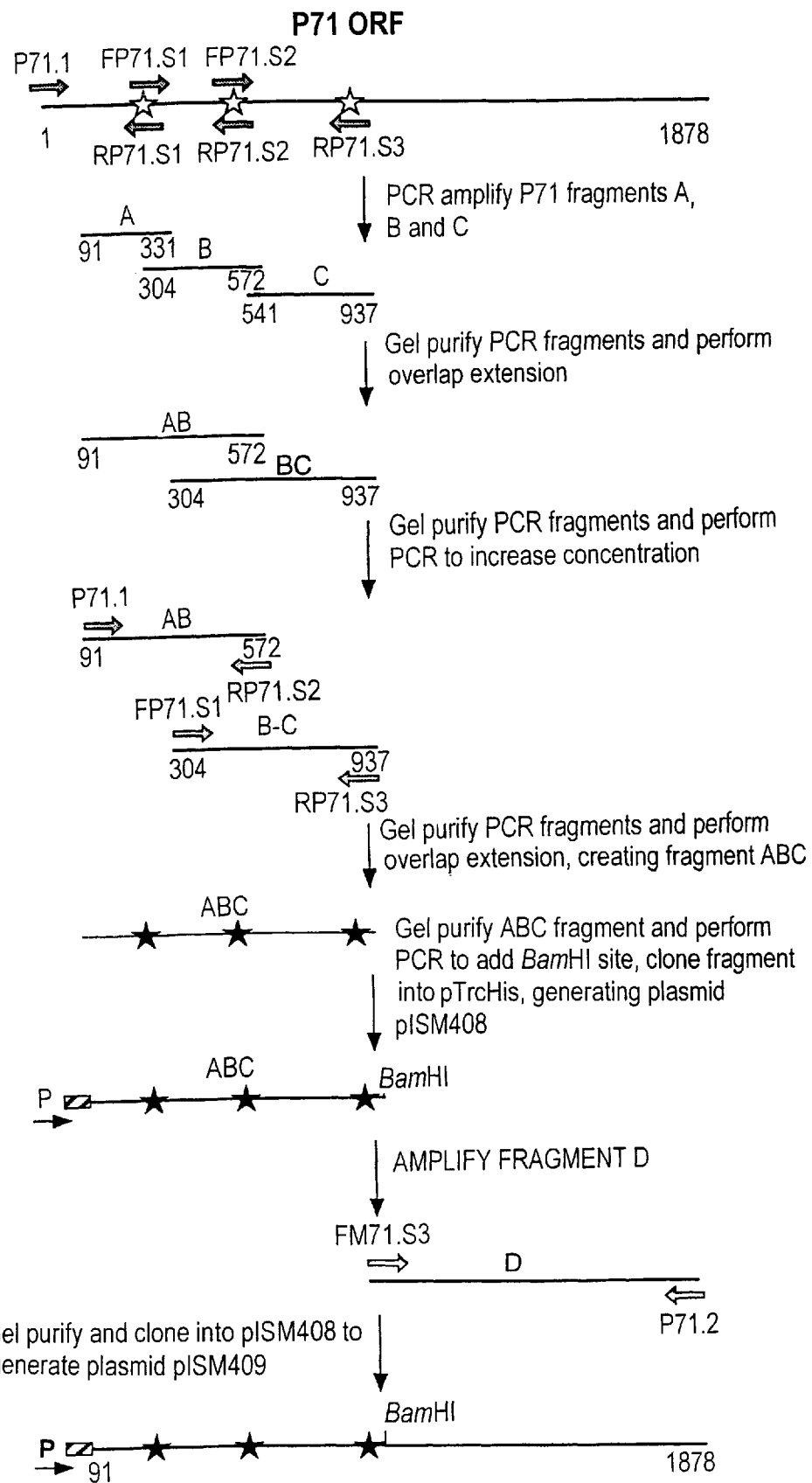
FIG. 4 is a diagrammatic depiction of the strategy used to replace the TGA codons in *Mycoplasma hyopneumoniae* P71-encoding cDNA that encode tryptophan in mycoplasma with TGG codons. The unfilled stars indicate the positions of TGA codons and the filled arrows indicate the position of TGG codons. Fragment designations are shown above each fragment. The position of the polyhistidine sequence and the promoter of the pTrcHis B plasmid are indicated by a hatched box and the letter "P", respectively.
Figure 5:
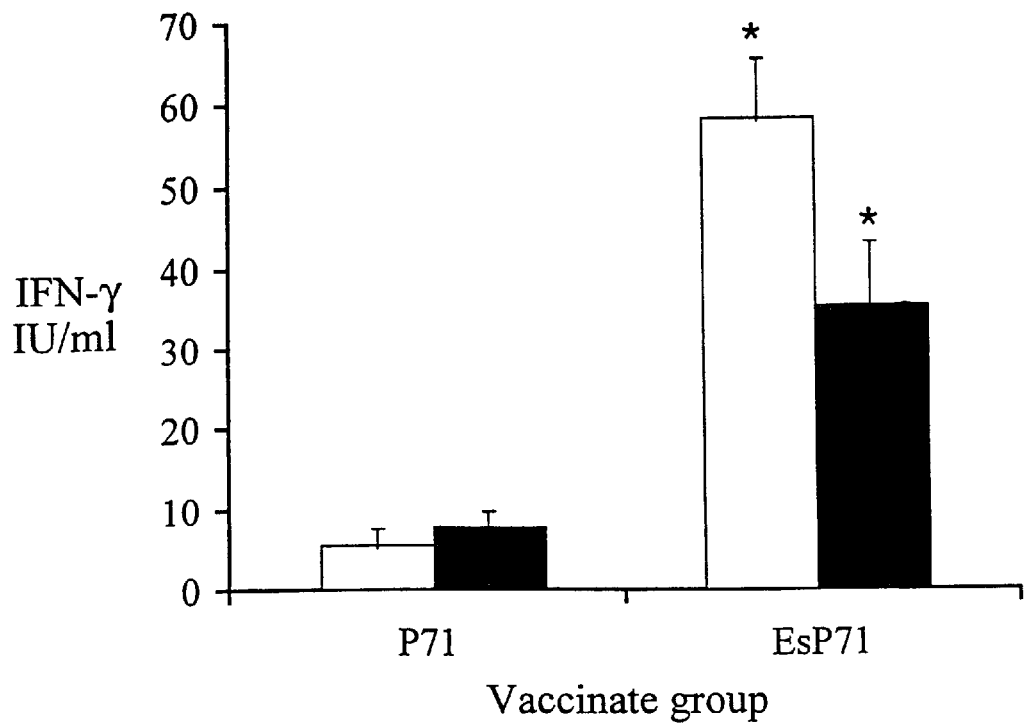
FIG. 5 is a bar graph showing the level of in vitro interferon-γ (IFN-γ) production in response to P71d by splenocytes from mice 32 days (unfilled bars) and 42 days (filled bars) after injection with vectors expressing P71d ("P721") or EsP71 ("EsP71").
Figure 6:
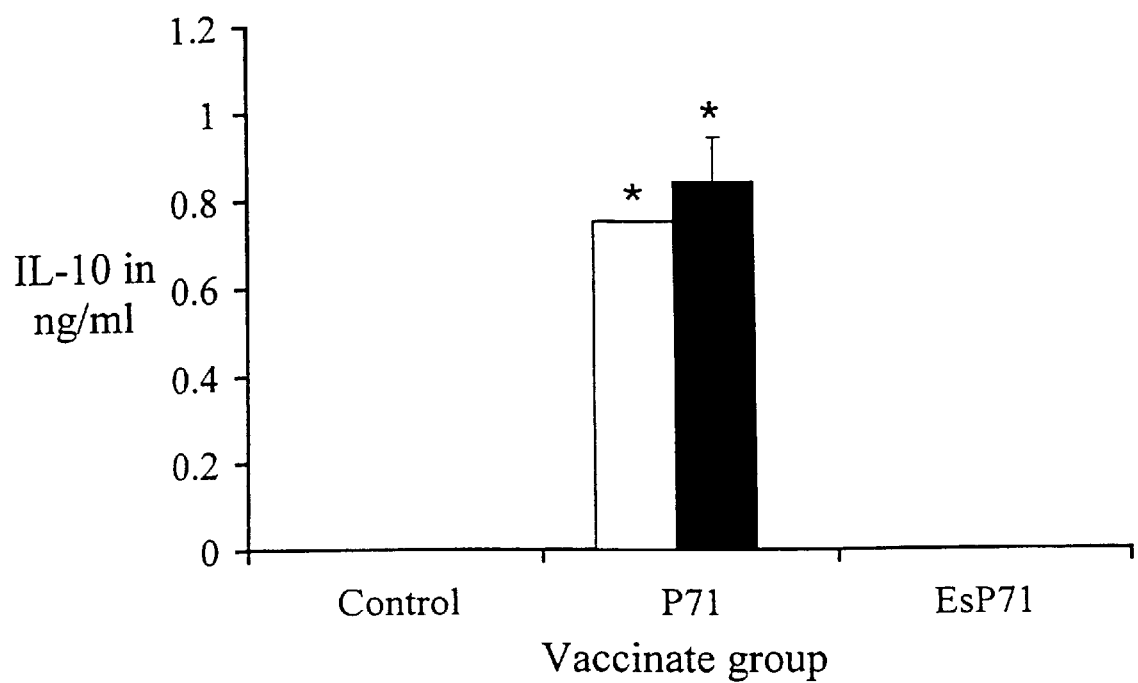
FIG. 6 is a bar graph showing the level of in vitro interleukin-10 (IL-10) production in response to P71d by splenocytes from mice 32 days (unfilled bars) and 42 days (filled bars) after injection with vectors expressing P71d ("P721") or EsP71 ("EsP71").
Figure 7:
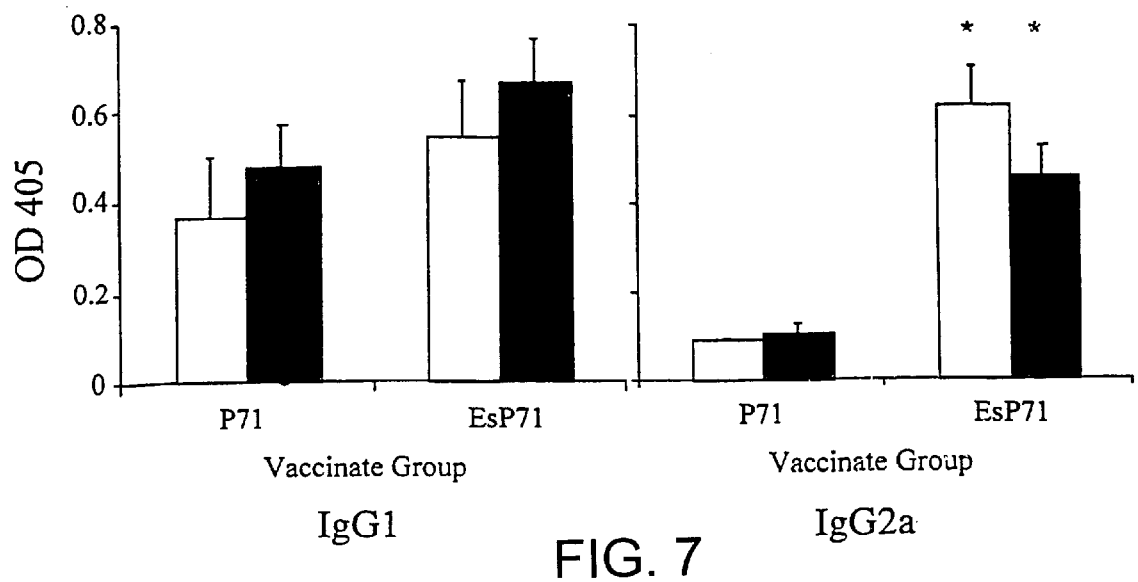
FIG. 7 is a pair of bar graphs showing the level of IgG1 and IgG2a antibody specific for P71d in serum harvested from mice 32 days (unfilled bars) and 42 days (filled bars) after injection with vectors expressing P71d ("P721") or EsP71 ("EsP71").
Figure 8:
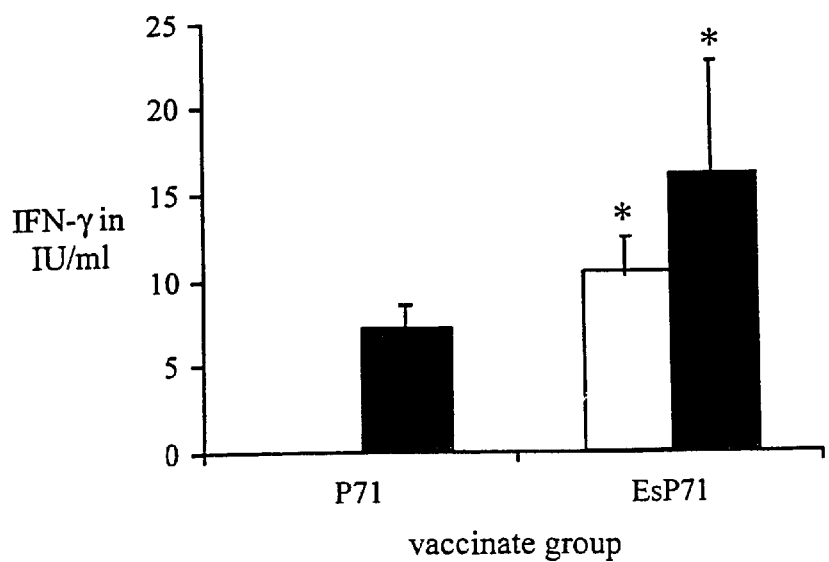
FIG. 8 is a bar graph showing the level of in vitro IFN-γ production in response to P71d by splenocytes from mice 25 days (unfilled bars) and 35 days (filled bars) after injection with P71d ("P721") or EsP71 ("EsP71").
Figure 9:
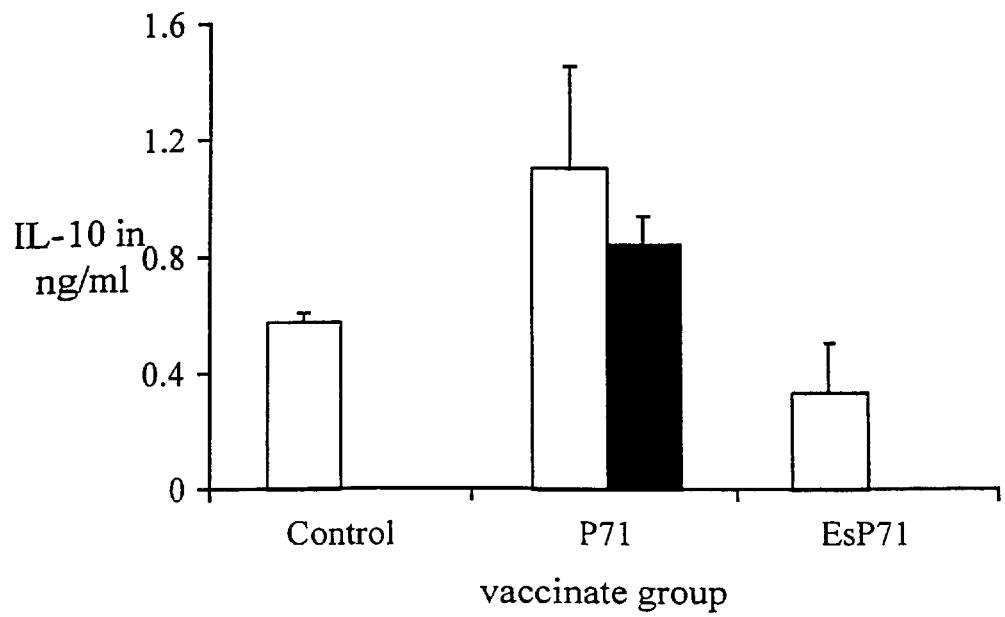
FIG. 9 is a bar graph showing the level of in vitro IL-10 production in response to P71d by splenocytes from mice 25 days (unfilled bars) and 35 days (filled bars) after injection with P71d ("P721") or EsP71 ("EsP71").
Figure 10:
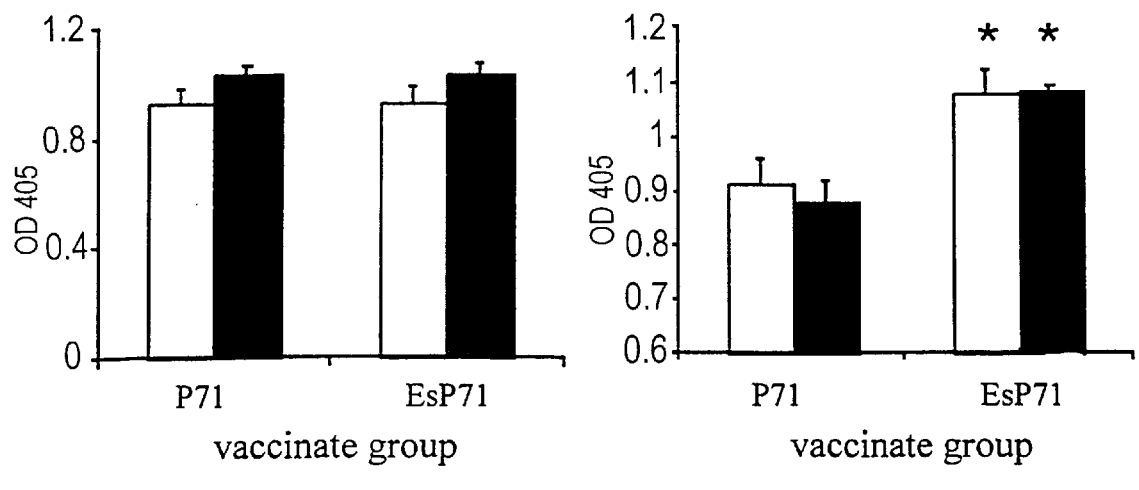
FIG. 10 is a pair of bar graphs showing the level of IgG1 and IgG2a antibody specified for P71d in serum harvested from mice 25 days (unfilled bars) and 35 days (filled bars) after injection with P71d ("P721") or EsP71 ("EsP71").

Site-Directed Mutagenesis of P71 gene sequence. Site-directed mutagenesis was performed by overlap extension PCR to convert TGA codons to TGG codons in the P71 gene sequence [Ge et al. Biotechniques 1997; 22: 28–30]. Complimentary primers were designed with the TGA codon substituted with TGG within the primer sequences and the optimum reaction parameters defined using Oligo primer analysis software (National Biosciences, Inc., Plymouth, Minn.). The strategy involved the joining of the PCR-generated overlapping fragments having the required mutations by several rounds of overlap extension and polymerase chain reactions (FIG. 4). All PCR reactions were performed using Pfu DNA polymerase following standard protocols. The final plasmid containing the modified P71 sequence ("P71d") was designated pISM409.

Plasmid preparations. Plasmid DNA for general purposes was isolated from *E. coli* according to the method of Birnboim [Birnboim H. (1983) Methods Enzymol 100: 243–55]. For sequencing, plasmid DNAs were prepared using the Qiagen midi-plasmid purification kit (QIAGEN Inc., Chatsworth, Calif.) according to the manufacturer's instructions. For genetic vaccinations, plasmid DNA was prepared using the Qiagen EndoFre Plasmid Giga Kit. The plasmid DNA was dissolved in endotoxin-free saline by overnight suspension at 4° C.

Purification of recombinant proteins. The p TrcHis B plasmid-derived constructs (pISM403, pISM409, and pISM410) were transformed into *E. coli* TOP 10 cells for expression of recombinant proteins. Individual colonies were inoculated into SB medium (32 g tryptone, 20- g yeast extract, 5 g NaCl per liter) containing 100 μg ampicillin per ml and incubated at 37° C. in floor shaker for 6 h. Each culture was subcultured into a 100 X volume of SB medium containing ampicillin (100 μg per ml) and incubated at 37° C. with vigorous shaking until the $OD_{600}$ was approximately 0.6. At that point, the incubating temperature was lowered to 30° C., and isopropyl thio-β-D-galactopyranoside (IPTG) (for induction) and phenyl methyl sulfonyl fluoride (PMSF) (to inhibit proteolysis) were added to a final concentration of 1 mM and 0.05 mM, respectively. The bacterial culture was induced for 6 to 8 h, and then the cells were pelleted at 5,000 x g for 10 min at 4° C., and the pellets stored frozen at −20° C.

For protein purification, the induced bacterial cell pellet was thawed and resuspended in lysis buffer (20 mM Tris, 100 mM NaCl, 1 mg per ml lysozyme, pH 8.0). The suspension was incubated at room temperature for 30 min and subjected to two freeze-thaw cycles to lyse the cells using a dry ice/ethanol bath and a 50° C. water bath. The DNA was sheared by passing the sample several times through an 18 G needle. The sample was then centrifuged at 12,0000 x g for 20 min at 4° C. to pellet the insoluble material. Ten ml of Talon metal (cobalt) affinity resin (CLONTECH Laboratories, Inc., Palo Alto, Calif.) was washed with the basal buffer (20 mM Tris, 100 mM NaCl, pH 8.0) and the poly-histidine labeled protein was bound to the resin in batch mode.

Following resin washing and elution with basal buffer plus 500 mM imidazole, the protein was dialyzed against PBS and then against deionized water using SPECTRA/POR 3 dialysis membrane (SPECTRUM, Houston, Tex.) at 4° C. The dialyzed material was then freeze-dried, dissolved in water and stored in aliquots at −20° C. Purity was assessed using SDS-PAGE and immunoblot. Anti-Xpress antibodies (Invitrogen Corporation, San Diego, Calif.) were routinely used for detecting the recombinant proteins, but in some cases, antisera from P71d immunized mice were used. Lipopolysaccharide contamination was estimated using the Limulus Amebocyte Lysate (Bio Whittaker, Walkersville, Md.).

Genetic vaccination. Six to eight week old mycoplasma-free female BALB/c mice were immunized in groups of 6 with 100 μg of endotoxin free plasmid DNA in normal saline on day 0. Plasmids were injected intramuscularly into the thigh muscle of mice primed two days previously with 100 μl of 0.25% Bupivacaine. The identical booster dose on day 21 also followed another similarly time bupivacaine priming. The control mice were vaccinated with the vector plasmids not containing expressible inserts. Mice were housed at the Laboratory Animal Resource Facility, Iowa State University. All animal studies were conducted according to the guidelines of the Iowa State University Committee on Animal Care and Use.

Estimation of antigen-specific cytokine release. At necropsy on days 32 and 42, the mice were euthanized using $CO_2$ and exsanquinated by cardiac puncture. Spleens were removed aseptically using sterile instruments and transferred to a petri dish containing 5 ml of RPMI medium. Each excised spleen was dispersed into a single cell suspension, and the cells were washed once in RPMI medium and resuspended in complete RPMI (RPMI plus 10% fetal bovine serum and $5 \times 10^{-5}$ M β-mercaptoethanol). For cytokine analysis, cell cultures were set up in Costar 48 well tissue culture clusters with 5 million cells per well incubated were 10 μg per ml of purified recombinant P71d, EsP71 or ESAT-6. The negative control wells had cells alone in complete RPMI while the positive control wells were stimulated with 1 μg per ml of Concanavalin A. The supernatants were collected after 72 h and stored at −70° C.

The IFN-γ, IL-4 and IL-10 levels in culture supernatants were measured by a sandwich ELISA using a modified cytokine ELISA protocol. Immulon 2™ 96 well plates were coated with capture antibody [rat Mab XMG 1.2 for IFN-γ; rat Mab JES5-2A5 for IL-10; rat Mab 11B11 for IL-4 (PharMingen)] at 2 μg per ml in coating buffer overnight at 4° C., blocked with 1% gelatin for one h at 37° C., and then incubated with 100 μl of culture supernatant in triplicate wells diluted either 1:2 or 1:4 in basal RPMI for one h at 37° C. For IFN-γ estimation, the plates were then incubated with 100 μl of a 1:2,000 dilution of rabbit anti-mouse IFN-γ antibodies followed by incubation with 100 μl of alkaline phosphatase-conjugated donkey anti-rabbit Immunoglobulin. Plates were incubated with biotinylated rat anti-mouse IL-10 (SXC-1) or biotinylated rat anti-mouse IL-4 (BVD6-24G2) (PharMingen) at 1:2,000 dilution followed by alkaline phosphatase-conjugated strepavidin. The plates were washed with PBS-Tween after each incubation step. The plates were developed by the addition of alkaline phosphatase substrate and the developed color quantified by measuring the OD at 405 nm. The concentrations of IFN-γ, IL-4 and IL-10 in the culture supernatants were estimated from the standard curves generated using mouse rIFN-γ, rIL-4 and rIL-10 (PharMingen) for the average of duplicate wells.

Immunization with recombinant protein and in vitro assays for cytokine production.

Groups of 6 mycoplasma-free female BALB/c mice were immunized with purified proteins according to the following schedule. Equal molar amounts of ESAT-6 (1 μg), P71d (9 μg) or EsP71 (10 μg) were injected intramuscularly on day 0 and boosted with an identical dose on day 14. Three mice from each group were sacrificed on day 25 and three on day 35. The purified proteins were suspended in saline. The protein concentration was adjusted to provide an individual dose in 100 μl and was administered intramuscularly into the thigh muscle. The control mice were injected with normal saline. At necropsy, the mice were euthanized using $CO_2$ and exsanquinated by cardiac puncture. The blood was transferred into microcentrifuge tubes and allowed to clot at 4° C. Serum was collected the next day by centrifugation, transferred to another microcentrifuge tube, and stored at −20° C. Spleens were removed aseptically using sterile instruments and transferred to a petri dish containing 5 ml of RPMI medium.

Each excised spleen was dispersed into a single cell suspension and the cells were washed once in RPMI medium. The lymphocytes were counted and resuspended at a concentration of $5 \times 10^6$ cells per ml. Cell cultures were set up in complete RMPI and incubated at 37° C. in 5% $CO_2$ under relatively high humidity. For cytokine analysis, cells were cultured in 48 well tissue culture cluster dishes (Costar, Cambridge, Mass.) at $5 \times 10^6$ cells per well with 10 μg of the antigen of interest (ESAT-6, P71 d or EsP71). The negative control wells contained cells alone in complete RPMI while the positive control wells contained cells stimulated with 1 μg per ml Concanavalin A. The supernatants were collected after 72 h of incubation by centrifugation and stored at −70° C. until analyzed. Cytokine levels in the supernatants were measured as described above for DNA-immunized animals.

Quantitation of antigen-specific antibody responses. An ELISA was employed to measure antigen specific IgG1 and IgG2a antibody responses. Immulon $2^{HB}$ microtiter plates (Corning, Park Ridge, Ill) were coated with 0.2 μg per well of purified P71d protein diluted in carbonate buffer (2.93 g sodium bicarbonate, 1.5 g sodium carbonate, 0.2 g sodium azide per liter; pH 9.5) by overnight incubation at 4° C. After extensive washing, the coated plates were blocked with 1% gelatin in PBS (8 g NaCl, 1.5 g $Na_2HPO_4$, 0.2 g $KH_2PO_4$, 0.2 g KCl per liter, pH 7.4) for one hour. After further extensive washing of the plates, the serum samples were added to appropriate wells at a dilution of 1:100 in PBS and incubated at 37° C. for 1.5 hours. After additional extensive washing, the plates were incubated with isotype-specific alkaline phosphatase-conjugated goat anti-mouse IgG1 or IgG2a (1:1000) (Southern Biotechnology Associates, Birmingham, Ala.) for 1 h at 37° C. The plates were washed with PBS containing 0.5% Tween 20 (Sigma, St. Louis, Mo.), and then developed using alkaline phosphatase substrate (Sigma 140, Sigma). The optical density (OD) results were read at 405 nm and the date are presented as the average OD values of duplicate wells.

Statistical analysis. Statistical evaluations were performed by one-way analysis of variance or Mann Whitney test using InStat 2.0 (GraphPad Software, San Diego, Calif.).

Example 2

Identification, Analysis, and Site-directed Mutagenesis of P71 Gene Sequences

The screening of a M. hyopneumoniae λZAP II genomic library with convalescent pig sera resulted in the identification of an ORF encoding an immunogenic protein. Sequence analysis revealed an ORF coding for a 71-kDa protein, designated P71, and the presence of three TGA codons at positions 322, 553, and 925 within the coding sequence (FIG. 1).

To express P71 in vivo in a DNA vaccine vector or in E. coli, it was necessary to remove the TGA codons within the coding sequence and replace them with TGG. This was accomplished using overlap extension PCR as described in FIG. 4. A PCR-based protocol for site-directed mutagenesis of the P71 structural gene was chosen. Each step required the optimization of the PCR reaction conditions. PCR products were then mixed and extension reactions performed to obtain fragments with multiple modified UGA codons. The modified gene was originally cloned in two steps as shown in FIG. 4. The first step included insertion of the 5' end of the gene with all three modified TGA codons into pTrcHis B. A BamHI cloning site was placed downstream of the third TGA codon. This was accomplished by altering two base pairs of the sequence in the final PCR reaction resulting in a two amino acid change in the polypeptide sequence (i.e., $Asn^{280} \rightarrow Lys^{280}$ and $Ser^{282} \rightarrow Pro^{282}$). An identical change was incorporated into the 3' portion of the gene during the second PCR reaction (FIG. 4). This 3' fragment was then combined with the partial gene to generate plasmid pISM409, which contained the nucleotide sequence encoding P71, minus a 30 amino acid membrane-spanning domain and with the above amino acid changes. The pISM409 plasmid was used as a template to generate the P71-containing PCR fragment for construction of plasmids pISM410, pISM421 and pISM422.

Example 3

Plasmid Constructs and Immune Responses Following DNA Immunization

The complete ORF of ESAT-6 was cloned into plasmid pVR1020 generating plasmid pISM417. This plasmid served as the ESAT-6 control in genetic immunization experiments. Cloning of the ESAT-6 Bg/II-digested PCR fragment into the BamHI-digested pVR1020 resulted in the loss of the BamHI restriction sites in pISM417. To generate the intermediate EsP17 construct pISM418, the stop codon was removed from the reverse primer R2Es used for the generation of the ESAT-6 inserts. Necessary changes in the forward primer were incorporated to generate an in-frame protein sequence at the N terminus with the tissue plasminogen activator signal of pVR1020. Cloning of the double-digested BamHI and Bg/II PCR fragment required for generating the intermediate fusion construct pISM418 resulted in the regeneration of the BamHI site at the 5' end of the insert. This site was then used in the cloning of the PCR product containing the P71d coding sequence generating the EsP71 gene fusion.

Splenocytes from P71d and EsP71 vaccinates (i.e., mice injected with pISM421 and pISM422) showed significant ($p<0.01$) production of IFN-γ following stimulation with purified P71d protein (FIG. 5). The splenocytes from the EsP71 (pISM422) vaccinates produced significantly higher levels of IFN-γ on days 32 and 42 when compared to splenocytes from the pISM421 (P71d alone) vaccinates ($p<0.05$). The difference between the P71d and EsP71 vaccinates was about 10-fold on day 32, and it decreased to about 4–5 fold by day 42. There was not detectable IFN-γ in splenocyte cultures from mice immunized with pISM417 (ESAT-6 alone) or the control mice (saline) when stimulated with P71d (data not shown). There was also no detectable IFN-γ in splenocyte cultures from mice immunized with pISM421 (P71) when stimulated with either purified EsP71 or ESAT-6 protein (data not shown).

FIG. 6 shows the levels of IL-10 produced by stimulating splenocytes from the various mice with P71d. Only splenocytes from pISM421-immunized mice secreted IL-10 when stimulated with recombinant P71d protein (FIG. 6) ($p<0.01$). The IL-10 levels were 0.8 and 0.9 ng per ml on days 32 and 42, respectively.

FIG. 7 shows the relative levels of IgG1 and IgG2a antibodies specific for P71 produced by the various immunized mice. Not all of the mice seroconverted (as defined by two standard deviation units above the control level) (data not shown). For IgG1, four out of the six mice seroconverted on day 32 in the pISM421 (P71d) vaccinates and all six mice seroconverted by day 42. All the mice seroconverted in the pISM422 (EsP71) vaccinate group at both time points. There was an increase in IgG1 anti-P71 antibody in both P71 as well as EsP71 vaccinates from day 32 to day 42. The EsP71 vaccinates showed somewhat higher levels of IgG1 at both time points compared to the P71d vaccinates that were not significant. With respect to the IgG2a isotype, two of the P71d vaccinates seroconverted on day 32 while 5 out of the 6 seroconverted by day 42. All EsP71 vaccinates had seroconverted on both days. The IgG2a levels were significantly higher on both days 32 and 42 for EsP71 vaccinates compared to P71d vaccinates ($p<0.05$).

Example 4

Purification of Recombinant Proteins and Immune Responses Following Protein Immunization Purity of the recombinant protein preparations was assessed by immunoblot. These were routinely found to be greater than 95% pure. Lipopolysaccharide contamination of each preparation was less than 1 Endotoxin Unit per μg purified product, a level which would have no effect on mouse splenocyte responses.

To determine if ESAT-6 has an effect on P71-specific induction of IFN-γ, splenocytes from each group of immunized mice were stimulated with purified ESAT-6 or P71d protein in vitro, and the resulting culture supernatants were examined for IFN-γ levels by ELISA. When splenocytes from control or P71d vaccinates were stimulated with ESAT-6, no IFN-γ secretion was detected (data not shown). Thus, ESAT-6 did not stimulate non-specific IFN-γ secretion in unprimed lymphocytes. In addition, ESAT-6 vaccinates failed to secrete IFN-γ in response to ESAT-6 antigen (data not shown). In contrast, splenocytes from EsP71 vaccinates showed a response to ESAT-6 stimulation, but only on day 35 following the booster administration (13 IU per ml). When stimulated in vitro with purified P71d protein, splenocytes from mice vaccinated with recombinant EsP71 protein secreted 10 IU per ml of IFN-γ on day 25 and an increased amount on day 35 (FIG. 8). Splenocytes from P71d vaccinates failed to secrete IFN-γ response to P71d on day 25 and secreted significantly less than splenocytes from EsP71 vaccinates on day 35. Splenocytes from ESAT-6 vaccinate controls failed to secrete detectable levels of IFN-γ (data not shown) in response to P71d at either time point suggesting that ESAT-6 enhanced the IFN-γ response to P71d in EsP71 immunized lymphocytes.

When ESAT-6 was used to stimulate splenocytes from the four vaccinate groups, little to no IL-10 was detected (data not shown). When purified P71d was used, however, splenocytes from mice vaccinated with P71d secreted more than 3 times the amount of IL-10 than cells from mice vaccinated with EsP71 (FIG. 9). On day 35, IL-10 could be detected only in supernatants collected from splenocytes from P71d vaccinates. A similar pattern of IFN-γ and IL-10 responsiveness to the P 97 *M. hyopneumoniae* was seen in splenocytes from mice immunized with either the P97 protein or a fusion protein composed of ESAT-6 and P97.

When sera from the EsP71 vaccinated mice were tested by ELISA against P71d antigen, significant differences in IgG2a and IgG1 levels were observed. In the P71d and EsP71 vaccinates, all mice seroconverted for both IgG1 as well as IgG2a (FIG. 10). The IgG1 levels were approximately the same for both the P71d as well as EsP71 vaccinates on both day 25 and day 35. The IgG2a levels for the EsP71 vaccinates, however, were significantly higher ($p<0.05$) on both days compared to that for the P71d vaccinates indicating that the presence of ESAT-6 caused a shift in the IgG2a anti-P71 response.

Although the invention has been described with reference to the presently preferred embodiment, it should be understood that various modifications can be made without departing from the spirit of the invention. Accordingly, the invention is limited only by the following claims.

What is claimed is:

1. A fusion agent comprising a first domain and a second domain, wherein (a) the first domain comprises an immune enhancing molecule: and (b) the second domain comprises an immunogenic molecule, wherein the immunogenic molecule is a tumor antigen, an autoantigen, a molecule produced by a fungus, a molecule produced by a mycoplasma, a molecule produced by a yeast, a polypeptide encoded by a virus, or a molecule produced by a bacterium, wherein the bacterium is selected from the group consisting of *Salmonella enteriditis, Listeria monocytogenes, Mycobacteria leprae, Staphylococcus aureus, Escherichia coli, Streptococcus pneumoniae, Borrelia burgdorferi, Actinobacillus pleuropneumoniae, Helicobacter pylori, Neisseria meningitidis, Yersinia eneterocolitica, Bordetella pertussis*, and *Porphyromonas gingivalis*.

2. The fusion agent of claim 1, wherein the immune enhancing molecule is a protein or a function fragment of the protein.

3. The fusion agent of claim 2, wherein the protein is *Mycobacterium tuberculosis* Early Secretory Antigenic Target 6 (ESAT-6).

4. The fusion agent of claim 1, wherein the immunogenic molecule is a protein or a function fragment of the protein.

5. The fusion agent of claim 4, wherein the protein is a *Mycoplasma hyopneumoniae* P71 protein.

6. The fusion agent of claim 1, wherein the immune enhancing molecule is a polypeptide and the immunogenic molecule is a polypeptide.

7. The fusion agent of claim 1, further comprising one or more additional domains, wherein each of the additional domains comprise an immune enhancing molecule or an immunogenic molecule.

8. The fusion agent of claim 1 wherein the mycoplasma is *Mycoplasma hyopneumoniae*.

* * * * *

UNITED STATES PATENT AND TRADEMARK OFFICE
CERTIFICATE OF CORRECTION

PATENT NO. : 6,537,552 B1
DATED : March 25, 2003
INVENTOR(S) : Sreekumar A. Menon, F. Chris Minion and Gregory G. Mahairas It is certified that error appears in the above-identified patent and that said Letters Patent is hereby corrected as shown below:

Title page,
Item [60], Related U.S. Application Data, delete "60/160,429" and replace with -- 60/160,249 --.

Column 1,
Line 2, delete "60/160,429" and replace with -- 60/160,249 --.
Line 55, delete "gigivalis" and replace with -- gingivalis --.

Column 4,
Line 38, delete "specified" and replace with -- specific --.

Column 5,
Line 67, delete "eiptope" and replace with -- epitope --.

Column 7,
Line 33, delete "gigivalis" and replace with -- gingivalis --.

Column 19,
Line 66, delete "37ºC." and replace with -- 37ºC --.

Column 20,
Line 2, delete "C." and replace with -- C --.
Line 4, delete "30ºC." and replace with -- 30ºC --.
Lines 9 and 19, delete "4ºC." and replace with -- 4ºC --.
Line 16, delete "50ºC." and replace with -- 50ºC --.
Line 19, delete "12,0000" and replace with -- 12,000 --.

Column 21,
Line 7, delete "4ºC." and replace with -- 4ºC --.
Line 7, delete "37ºC." and replace with -- 37ºC --.

Column 22,
Line 12, delete "37ºC." and replace with -- 4ºC --.
Line 21, delete "date" and replace with -- data --.

Column 23,
Line 34, delete "not" and replace with -- no --.

UNITED STATES PATENT AND TRADEMARK OFFICE
CERTIFICATE OF CORRECTION

PATENT NO.    : 6,537,552 B1
DATED         : March 25, 2003
INVENTOR(S)   : Sreekumar A. Menon, F. Chris Minion and Gregory G. Mahairas It is certified that error appears in the above-identified patent and that said Letters Patent is hereby corrected as shown below:

<u>Column 35,</u>
Line 10, delete "function" and replace with -- functional --.

Signed and Sealed this

Thirtieth Day of December, 2003

JAMES E. ROGAN
*Director of the United States Patent and Trademark Office*